(12) United States Patent
Ruschke et al.

(10) Patent No.: US 7,520,489 B2
(45) Date of Patent: Apr. 21, 2009

(54) FLUID HANDLING DEVICE AND METHOD OF MAKING SAME

(75) Inventors: Ricky R. Ruschke, Woodstock, IL (US); Edward Kandel, McHenry, IL (US); Michael G. Leonhard, West Bend, WI (US); Mark A. Kinsley, Lake Geneva, WI (US); John A. Leahey, Woodstock, IL (US); Jan W. M. Mijers, Haarlem (NL); Ronald J. Kay, Barrington, IL (US)

(73) Assignee: Filtertek Inc., Hebron, IL (US)

( * ) Notice: Subject to any disclaimer, the term of this patent is extended or adjusted under 35 U.S.C. 154(b) by 371 days.

(21) Appl. No.: 10/559,992

(22) PCT Filed: Jun. 17, 2004

(86) PCT No.: PCT/US2004/019641

§ 371 (c)(1),
(2), (4) Date: Dec. 7, 2005

(87) PCT Pub. No.: WO2004/112866

PCT Pub. Date: Dec. 29, 2004

(65) Prior Publication Data

US 2006/0163515 A1    Jul. 27, 2006

Related U.S. Application Data

(60) Provisional application No. 60/479,403, filed on Jun. 17, 2003.

(51) Int. Cl.
*F16K 51/00* (2006.01)
*F16L 29/00* (2006.01)
*F16L 37/28* (2006.01)

(52) U.S. Cl. .............. 251/149.7; 251/149.1; 604/249; 604/256

(58) Field of Classification Search ............ 251/149.1, 251/149.6, 149.7
See application file for complete search history.

(56) References Cited

U.S. PATENT DOCUMENTS 2,208,286 A    7/1940    Berger (Continued)

FOREIGN PATENT DOCUMENTS

DE    8 104 048 UU    7/1981

(Continued)

OTHER PUBLICATIONS

Braun, Product Profiles, Needle-Free, Ultrasite, http://www.bbraunusa.com/products/ultrasite.htm, 1 page (Oct. 29, 2002)

(Continued)

*Primary Examiner*—John K Fristoe, Jr.
(74) *Attorney, Agent, or Firm*—Brinks Hofer Gilson & Lione; Steven P. Shurtz

(57) ABSTRACT

A fluid handling device, such as a needlefree access device, includes a housing having an inlet and an inlet channel; and a flow control member comprising a combination outlet, biasing and piston member. The flow control member includes a piston section moveable between a closed position in which the piston section is inside the housing below the inlet channel but allows fluid to flow through the inlet channel; a biasing section connected to the piston section that normally biases the piston section into the inlet channel; and an outlet section connected to the biasing section having an outlet fitting in fluid communication with the inside of the housing.

56 Claims, 18 Drawing Sheets

U.S. PATENT DOCUMENTS

| | | | |
|---|---|---|---|
| 2,451,441 A | 10/1948 | Main, Jr. | |
| 2,999,499 A | 9/1961 | Willet | |
| 3,352,531 A | 11/1967 | Kilmarx | |
| 3,416,567 A | 12/1968 | von Dardel et al. | |
| 3,837,381 A | 9/1974 | Arroyo | |
| 3,841,354 A | 10/1974 | McDonnell | |
| 3,994,293 A | 11/1976 | Ferro | |
| 4,063,555 A | 12/1977 | Ulinder | |
| 4,121,585 A | 10/1978 | Becker, Jr. | |
| 4,143,853 A | 3/1979 | Abramson | |
| 4,176,683 A | 12/1979 | Leibinsohn | |
| 4,286,628 A | 9/1981 | Paradis et al. | |
| 4,333,455 A | 6/1982 | Bodicky | |
| 4,344,549 A | 8/1982 | Paradis et al. | |
| 4,369,812 A | 1/1983 | Paradis et al. | |
| 4,410,096 A | 10/1983 | Paradis | |
| 4,415,003 A | 11/1983 | Paradis et al. | |
| 4,444,335 A | 4/1984 | Wood et al. | |
| 4,496,348 A | 1/1985 | Genese et al. | |
| 4,534,464 A | 8/1985 | Lankton | |
| 4,535,820 A | 8/1985 | Raines | |
| 4,573,242 A | 3/1986 | Lankton et al. | |
| 4,585,435 A | 4/1986 | Vaillancourt | |
| D283,674 S | 5/1986 | Paradis et al. | |
| 4,596,557 A | 6/1986 | Pexa | |
| 4,610,276 A | 9/1986 | Paradis et al. | |
| 4,615,693 A | 10/1986 | Paradis et al. | |
| 4,634,434 A | 1/1987 | Marino, Jr. et al. | |
| 4,661,110 A | 4/1987 | Fortier et al. | |
| 4,683,905 A | 8/1987 | Vigneau et al. | |
| 4,710,168 A | 12/1987 | Schwab et al. | |
| 4,711,621 A | 12/1987 | Schomblond | |
| 4,737,334 A | 4/1988 | Folding et al. | |
| 4,744,741 A | 5/1988 | Glover et al. | |
| 4,749,003 A | 6/1988 | Leason | |
| 4,752,287 A | 6/1988 | Kurtz et al. | |
| 4,752,292 A | 6/1988 | Lopez et al. | |
| D296,592 S | 7/1988 | Wellenstam | |
| 4,778,453 A | 10/1988 | Lopez | |
| 4,782,841 A | 11/1988 | Lopez | |
| 4,793,351 A | 12/1988 | Landman et al. | |
| 4,816,020 A | 3/1989 | Brownell | |
| 4,816,024 A | 3/1989 | Sitar et al. | |
| 4,819,659 A | 4/1989 | Sitar | |
| 4,834,716 A | 5/1989 | Ogle, II | |
| 4,846,805 A | 7/1989 | Sitar | |
| 4,874,377 A | 10/1989 | Newgard et al. | |
| 4,915,687 A | 4/1990 | Sivert | |
| 4,917,668 A | 4/1990 | Haindl | |
| 4,931,048 A | 6/1990 | Lopez | |
| 4,935,010 A | 6/1990 | Cox et al. | |
| 4,946,448 A | 8/1990 | Richmond | |
| 4,954,130 A | 9/1990 | Edwards | |
| 4,983,344 A | 1/1991 | Brown | |
| 5,006,114 A | 4/1991 | Rogers et al. | |
| 5,008,060 A | 4/1991 | Kanai et al. | |
| 5,026,265 A | 6/1991 | Kanai et al. | |
| 5,048,537 A | 9/1991 | Messinger | |
| 5,049,128 A | 9/1991 | Duquette | |
| 5,070,905 A | 12/1991 | Paradis | |
| 5,078,683 A | 1/1992 | Sancoff et al. | |
| 5,080,652 A | 1/1992 | Sancoff et al. | |
| 5,083,741 A | 1/1992 | Sancoff | |
| D324,911 S | 3/1992 | Sancoff et al. | |
| 5,095,765 A | 3/1992 | Filbey et al. | |
| 5,105,983 A | 4/1992 | Sancoff et al. | |
| 5,120,324 A | 6/1992 | Sancoff | |
| 5,139,745 A | 8/1992 | Barr et al. | |
| 5,147,333 A | 9/1992 | Raines | |
| 5,165,874 A | 11/1992 | Sancoff et al. | |
| 5,179,983 A | 1/1993 | Cordner, Jr. et al. | |
| 5,180,380 A | 1/1993 | Pursley et al. | |
| 5,190,067 A | 3/1993 | Paradis et al. | |
| 5,196,203 A | 3/1993 | Boehm | |
| 5,199,947 A | 4/1993 | Lopez et al. | |
| 5,201,725 A | 4/1993 | Kling | |
| 5,202,128 A | 4/1993 | Morella et al. | |
| 5,203,775 A | 4/1993 | Frank et al. | |
| 5,207,667 A | 5/1993 | Walker et al. | |
| 5,213,115 A | 5/1993 | Zytkovicz et al. | |
| 5,221,268 A | 6/1993 | Barton et al. | |
| 5,224,934 A | 7/1993 | Payne et al. | |
| 5,230,706 A | 7/1993 | Duquette | |
| 5,242,393 A | 9/1993 | Brimhall et al. | |
| 5,242,432 A | 9/1993 | DeFrank | |
| 5,244,463 A | 9/1993 | Cordner, Jr. et al. | |
| 5,277,916 A | 1/1994 | Dwyer et al. | |
| 5,279,563 A | 1/1994 | Brucker et al. | |
| 5,281,206 A | 1/1994 | Lopez | |
| 5,284,481 A | 2/1994 | Soika et al. | |
| 5,308,334 A | 5/1994 | Sancoff | |
| 5,324,258 A | 6/1994 | Rohrbough | |
| 5,328,474 A | 7/1994 | Raines | |
| 5,330,450 A | 7/1994 | Lopez | |
| 5,330,766 A | 7/1994 | Morella et al. | |
| 5,338,314 A | 8/1994 | Ryan | |
| 5,342,326 A | 8/1994 | Peppel et al. | |
| 5,344,414 A | 9/1994 | Lopez et al. | |
| 5,352,201 A | 10/1994 | Jemmott | |
| 5,354,275 A | 10/1994 | Behnke et al. | |
| 5,360,413 A | 11/1994 | Leason et al. | |
| 5,378,474 A | 1/1995 | Morella et al. | |
| 5,392,778 A | 2/1995 | Horzewski | |
| 5,397,303 A | 3/1995 | Sancoff et al. | |
| 5,398,850 A | 3/1995 | Sancoff et al. | |
| 5,398,851 A | 3/1995 | Sancoff et al. | |
| D361,379 S | 8/1995 | Sancoff et al. | |
| D361,617 S | 8/1995 | Sancoff et al. | |
| 5,437,655 A | 8/1995 | Bartholomew | |
| 5,439,451 A | 8/1995 | Collinson et al. | |
| 5,456,668 A | 10/1995 | Ogle, II | |
| 5,464,091 A | 11/1995 | Callahan et al. | |
| 5,465,938 A | 11/1995 | Werge et al. | |
| 5,472,053 A | 12/1995 | Sullaway et al. | |
| 5,479,967 A | 1/1996 | Zytkovicz et al. | |
| 5,492,532 A | 2/1996 | Ryan et al. | |
| 5,509,433 A | 4/1996 | Paradis | |
| 5,535,785 A | 7/1996 | Werge et al. | |
| 5,549,566 A | 8/1996 | Elias et al. | |
| 5,553,741 A | 9/1996 | Sancoff et al. | |
| 5,558,255 A | 9/1996 | Sancoff et al. | |
| 5,571,261 A | 11/1996 | Sancoff et al. | |
| 5,573,506 A | 11/1996 | Vasko | |
| 5,573,516 A | 11/1996 | Tyner | |
| 5,578,005 A | 11/1996 | Sancoff et al. | |
| 5,588,556 A | 12/1996 | Sancoff et al. | |
| 5,609,248 A | 3/1997 | Rohrbough et al. | |
| 5,618,268 A | 4/1997 | Raines et al. | |
| 5,620,427 A | 4/1997 | Werschmidt et al. | |
| 5,623,969 A | 4/1997 | Raines | |
| 5,641,021 A | 6/1997 | Murray et al. | |
| 5,647,434 A | 7/1997 | Sullaway et al. | |
| 5,676,346 A | 10/1997 | Leinsing | |
| 5,685,866 A | 11/1997 | Lopez | |
| 5,688,254 A | 11/1997 | Lopez et al. | |
| 5,690,612 A | 11/1997 | Lopez et al. | |
| 5,694,686 A | 12/1997 | Lopez | |
| 5,695,466 A | 12/1997 | Lopez | |
| 5,699,821 A | 12/1997 | Paradis | |
| 5,700,248 A | 12/1997 | Lopez | |
| 5,730,418 A | 3/1998 | Feith et al. | |
| D393,722 S | 4/1998 | Fangrow, Jr. et al. | |
| 5,738,663 A | 4/1998 | Lopez | |
| 5,741,121 A | 4/1998 | O'Leary | |

| | | |
|---|---|---|
| 5,746,414 A | 5/1998 | Weldon et al. |
| 5,771,935 A | 6/1998 | Myers |
| RE35,841 E | 7/1998 | Frank et al. |
| 5,775,671 A | 7/1998 | Cote, Sr. |
| 5,776,116 A | 7/1998 | Lopez et al. |
| 5,782,816 A | 7/1998 | Werschmidt et al. |
| 5,800,836 A | 9/1998 | Morella et al. |
| 5,806,831 A | 9/1998 | Paradis |
| 5,807,579 A | 9/1998 | Vilkov et al. |
| 5,810,768 A | 9/1998 | Lopez |
| 5,810,792 A | 9/1998 | Fangrow, Jr. et al. |
| 5,819,775 A | 10/1998 | Holloway |
| 5,820,604 A | 10/1998 | Fox et al. |
| 5,826,621 A | 10/1998 | Jemmott |
| 5,834,024 A | 11/1998 | Heinicke et al. |
| 5,839,715 A | 11/1998 | Leinsing |
| 5,865,813 A | 2/1999 | DeKalb et al. |
| 5,873,862 A | 2/1999 | Lopez |
| D410,081 S | 5/1999 | Sweeney et al. |
| 5,901,942 A | 5/1999 | Lopez |
| 5,928,204 A | 7/1999 | Lopez |
| 5,954,708 A | 9/1999 | Lopez et al. |
| 5,967,484 A | 10/1999 | Morris |
| 5,971,950 A | 10/1999 | Lopez et al. |
| D416,806 S | 11/1999 | Zimmer et al. |
| 5,976,115 A | 11/1999 | Parris et al. |
| 5,997,518 A | 12/1999 | Laibovitz et al. |
| 6,019,748 A | 2/2000 | Lopez |
| 6,033,687 A | 3/2000 | Heinicke et al. |
| 6,039,302 A | 3/2000 | Cote, Sr. et al. |
| 6,050,978 A | 4/2000 | Orr et al. |
| 6,051,176 A | 4/2000 | Boucherie |
| 6,066,117 A | 5/2000 | Fox et al. |
| 6,068,011 A | 5/2000 | Paradis |
| 6,074,366 A | 6/2000 | Rogers et al. |
| 6,083,194 A | 7/2000 | Lopez |
| 6,117,114 A | 9/2000 | Paradis |
| 6,132,403 A | 10/2000 | Lopez |
| 6,132,404 A | 10/2000 | Lopez |
| 6,142,446 A | 11/2000 | Leinsing |
| 6,152,900 A | 11/2000 | Mayer |
| 6,168,137 B1 | 1/2001 | Paradis |
| 6,170,800 B1 | 1/2001 | Meloul et al. |
| 6,189,859 B1 | 2/2001 | Rohrbough et al. |
| 6,194,000 B1 | 2/2001 | Smith et al. |
| 6,197,348 B1 | 3/2001 | Morella et al. |
| 6,228,069 B1 | 5/2001 | Barth et al. |
| 6,245,048 B1 | 6/2001 | Fangrow, Jr. et al. |
| 6,260,890 B1 | 7/2001 | Mason |
| 6,264,313 B1 | 7/2001 | Mackowiak et al. |
| 6,287,289 B1 * | 9/2001 | Niedospial, Jr. ............ 604/408 |
| 6,290,206 B1 | 9/2001 | Doyle |
| 6,325,781 B1 | 12/2001 | Takagi et al. |
| 6,344,033 B1 | 2/2002 | Jepson et al. |
| 6,428,520 B1 | 8/2002 | Lopez et al. |
| 6,471,674 B1 | 10/2002 | Emig et al. |
| 6,482,188 B1 | 11/2002 | Rogers et al. |
| D468,016 S | 12/2002 | Mosler et al. |
| 6,491,668 B1 | 12/2002 | Paradis |
| 6,527,729 B1 | 3/2003 | Turcott |
| 6,541,802 B2 | 4/2003 | Doyle |
| 6,651,956 B2 | 11/2003 | Miller |
| 6,669,673 B2 | 12/2003 | Lopez |
| 6,682,509 B2 | 1/2004 | Lopez |
| 6,776,597 B2 | 8/2004 | Buhler |
| 6,802,490 B2 | 10/2004 | Leinsing et al. |
| 6,871,838 B2 | 3/2005 | Raines et al. |
| 7,104,520 B2 | 9/2006 | Leinsing et al. |
| 7,184,825 B2 | 2/2007 | Leinsing et al. |
| 2001/0049508 A1 | 12/2001 | Fangrow, Jr. et al. |
| 2002/0024036 A1 | 2/2002 | Rohrbough et al. |
| 2006/0178645 A1 | 8/2006 | Peppel |

FOREIGN PATENT DOCUMENTS

| | | |
|---|---|---|
| DE | 3 132 323 A1 | 4/1983 |
| DE | 3 303 073 C1 | 9/1984 |
| EP | 0 015 443 A1 | 9/1980 |
| EP | 0 309 771 A1 | 4/1989 |
| EP | 0 629 418 | 12/1994 |
| WO | WO 93/11828 A1 | 6/1993 |
| WO | WO 02/04065 A2 | 1/2002 |
| WO | WO 2004/112866 | 8/2004 |

OTHER PUBLICATIONS

B/Braun, Needle-Free Systems, http://www.bbraunusa.com/index.cfm?uuid=096405BED0B759A1E3EE1C06A2002023, 3 pages (May 26, 2004).
B. Braun Ultrasite System, Chapter 3. Evaluations, Needleless IV Systems, p. 106 (2001).
Halkey-Roberts, New Products—Medical, Swabable Luer Valves; http://www.halkey-roberts.com/NewProds/NewProds1.htm, 1 page (Jan. 24, 2005).
Halkey-Roberts, Medical Products—Activated Valves, http://www.halkey-roberts.com/listprod.asp?pic=1&ID=5 &cat=Medical+Products, 1 page (Jan. 24, 2005).
Halkey-Roberts, Robertsite Needleless Injection Site, 25 pages (Oct. 2003).
Krauss-Maffei Two Shot Revolution presentation slides, 23 pages (prior to Jun. 17, 2003).
Martin, C., "Disposable Filling Methods," *Medical Design Technology*, 3 pages (Dec. 2005).
Millam, Doris, "Avoiding Needle-Stick Injuries," 20(1) *Nursing* 61-64 (Jan. 1990).
Nimmer, T., et al., "Making Ink and Labels Stick to Plastic," *Packaging Design Engineer*, 4 pages (Feb. 2004).
Ogando, J., "Liquid Injection Molding Hits Its Stride," *Plastics Technology*, 5 pages (Oct. 1999).
Spotlight, Treatment and Symptom Control, *Oncology Nurse Bulletin*, 7 pages (Oct. 1988).

* cited by examiner

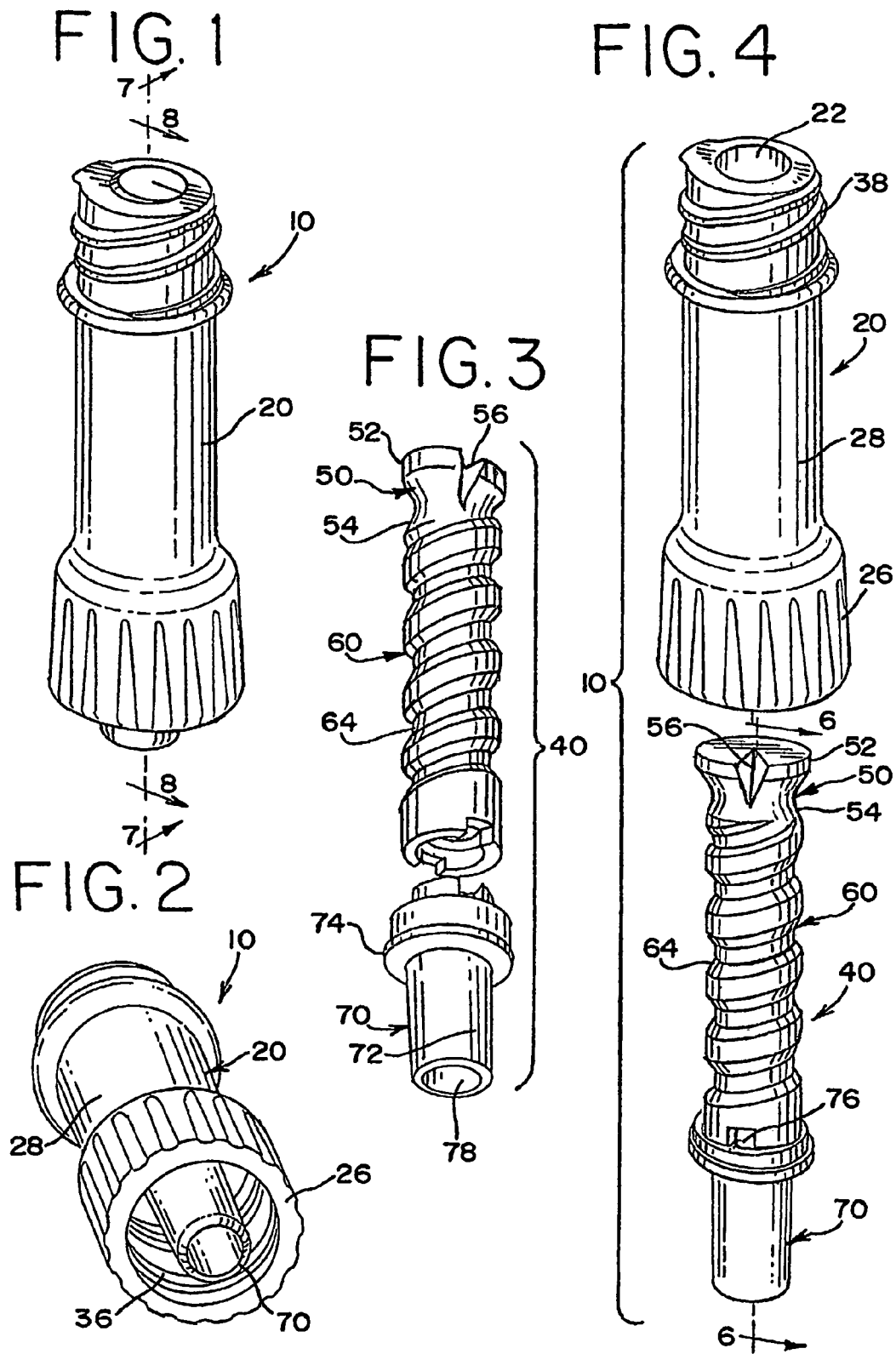

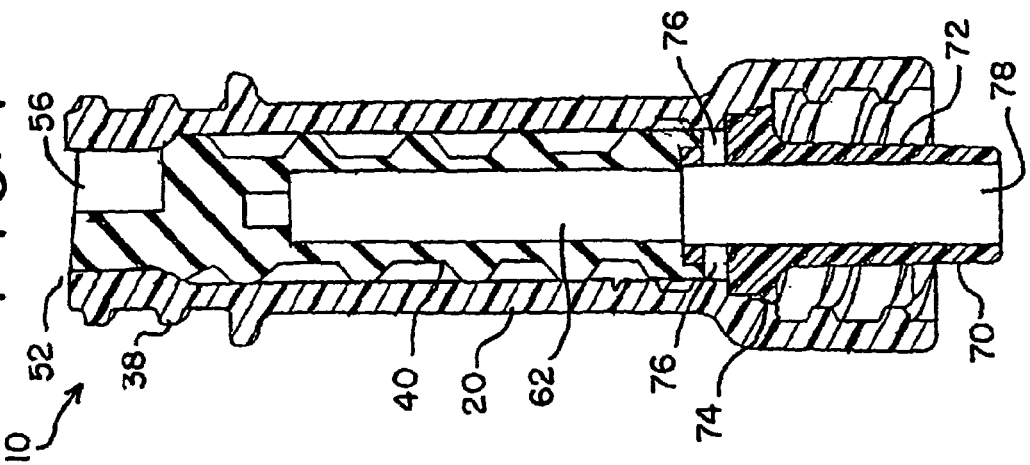
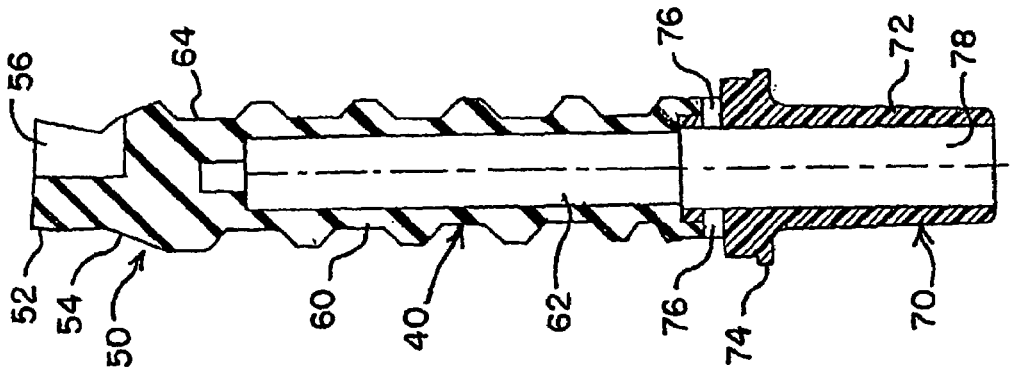
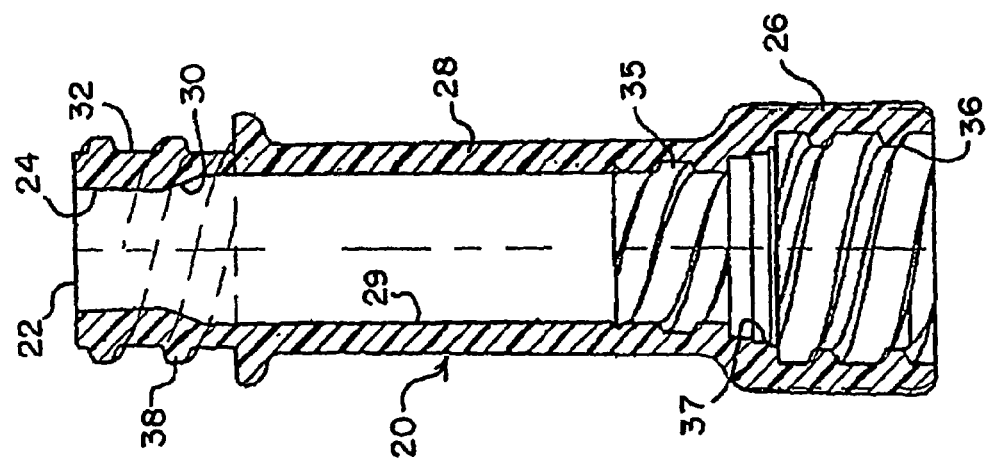

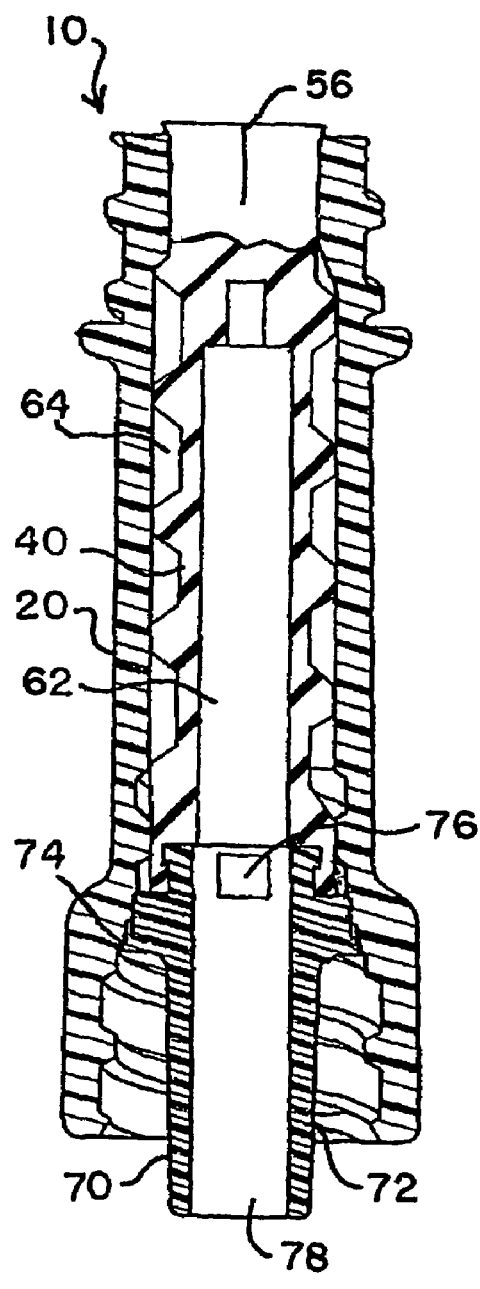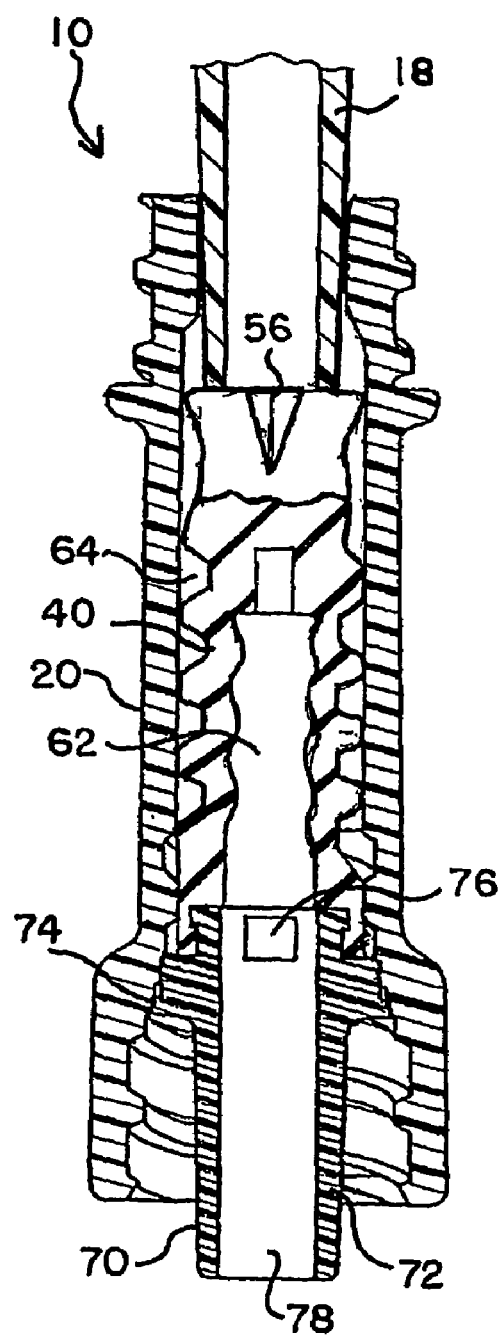

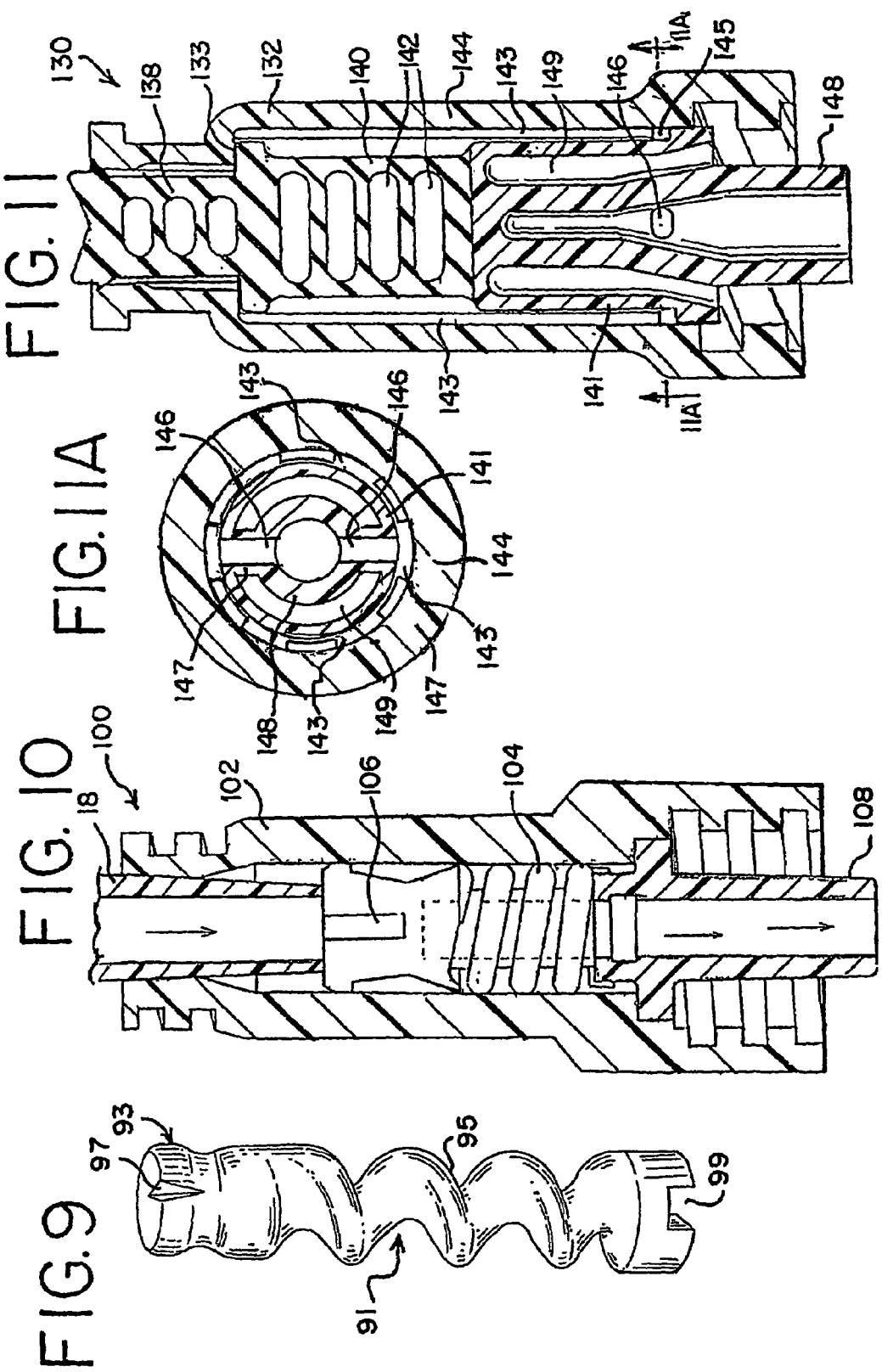

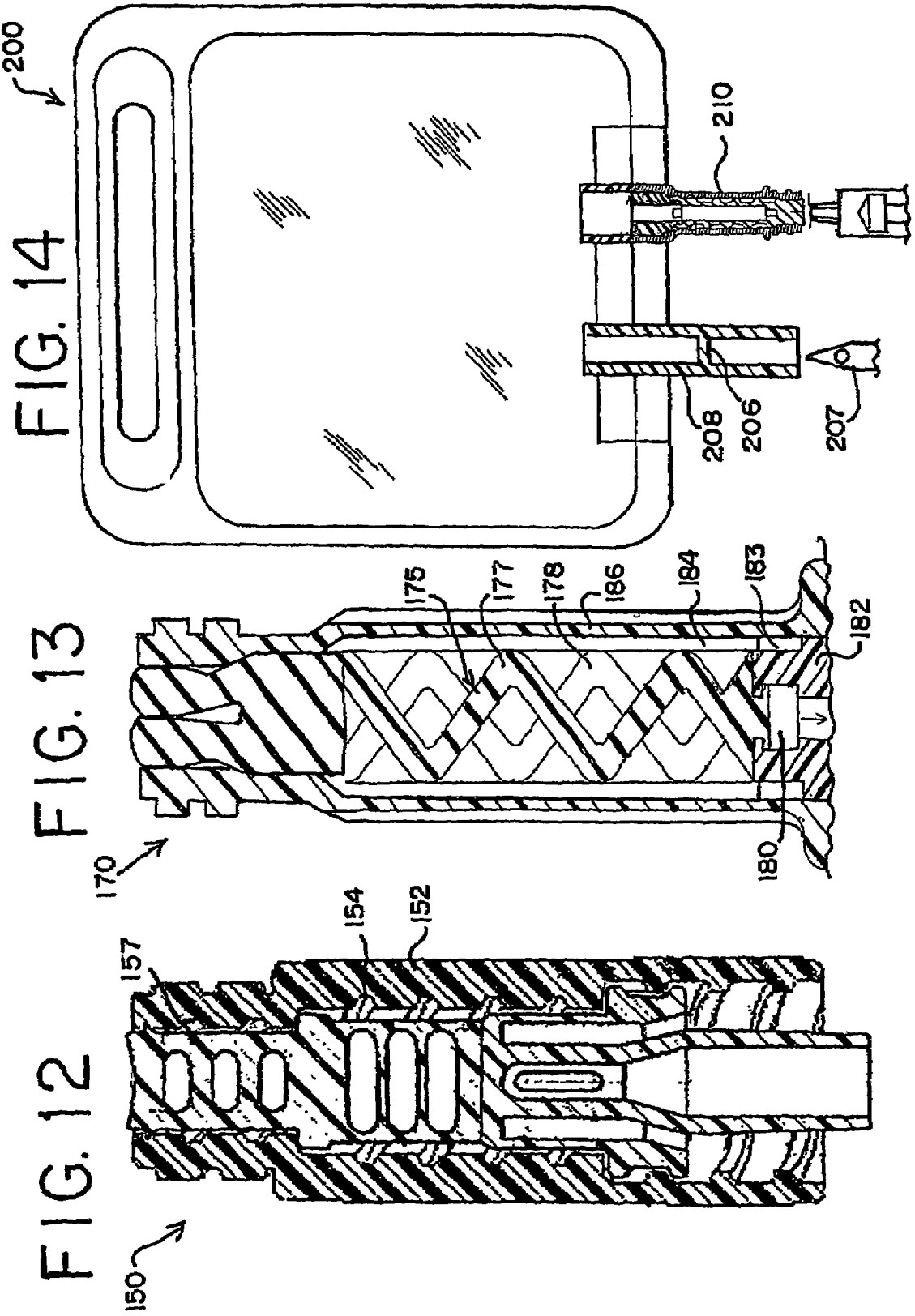

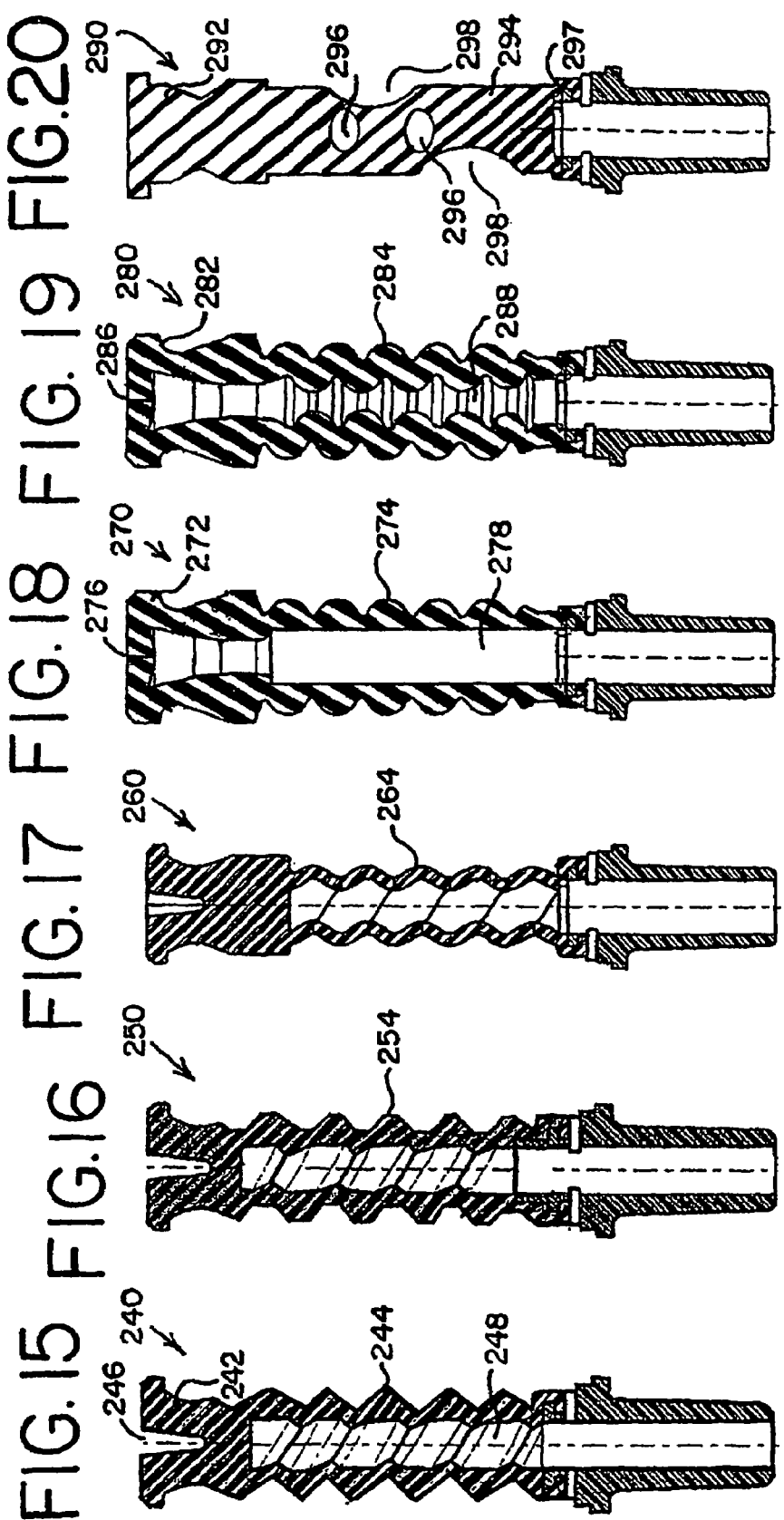

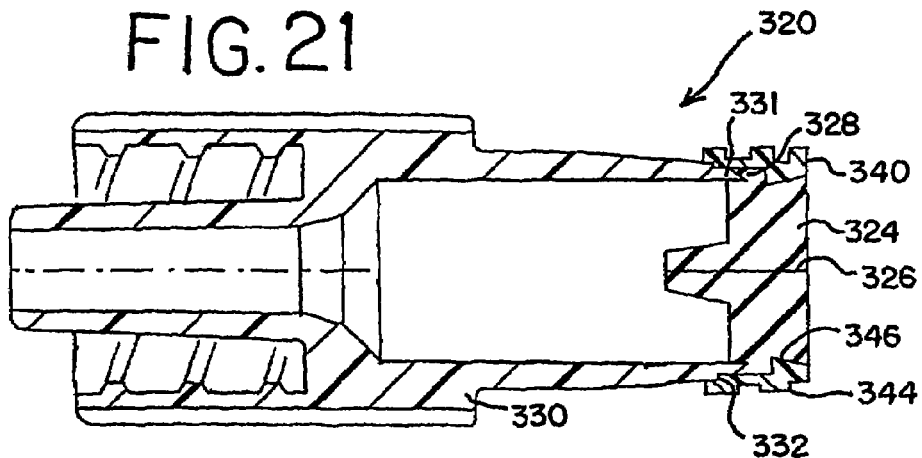
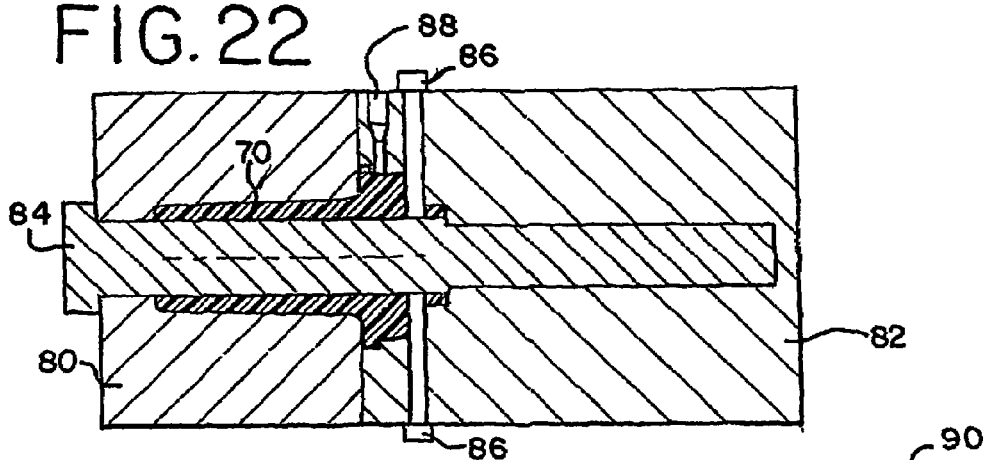
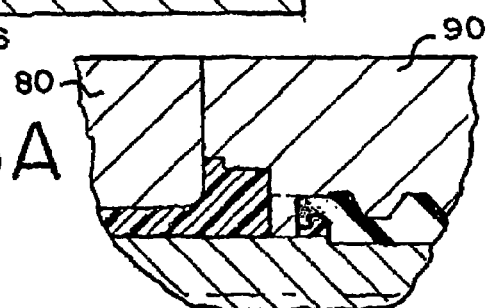
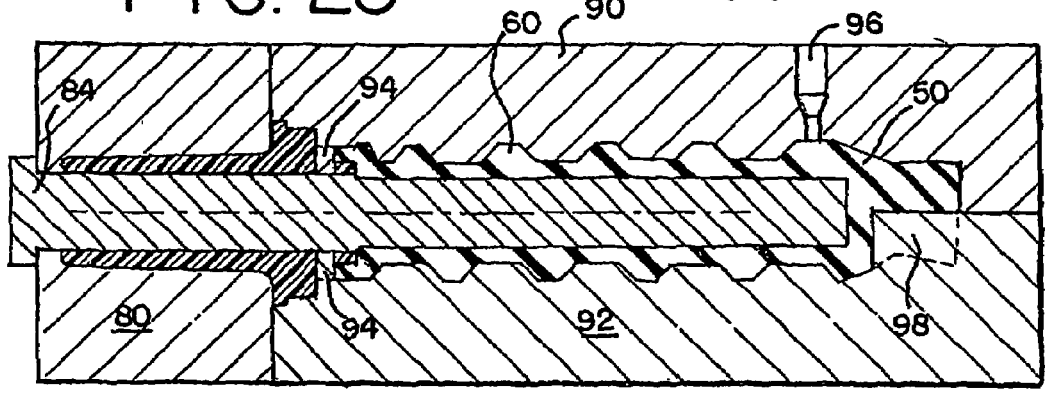

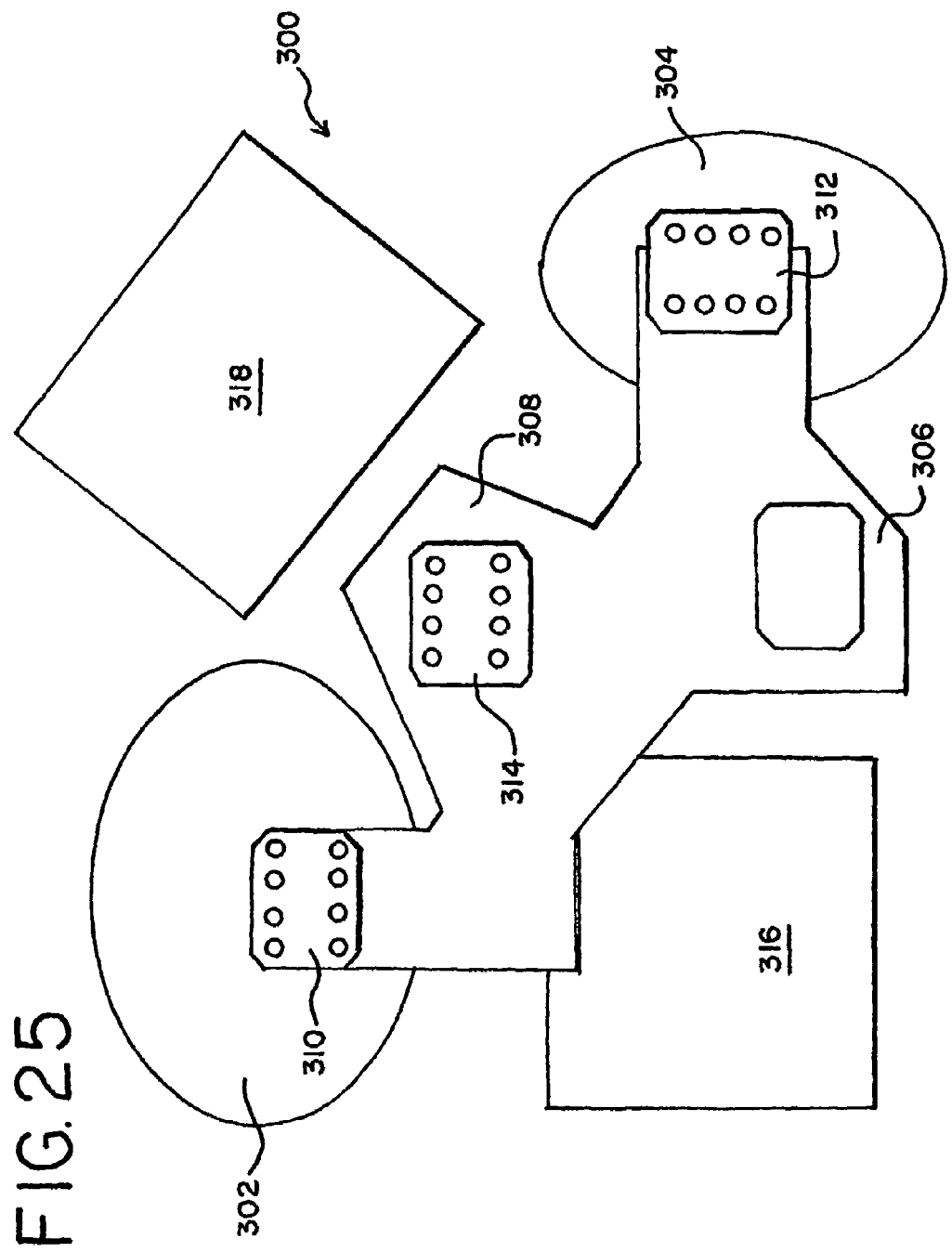

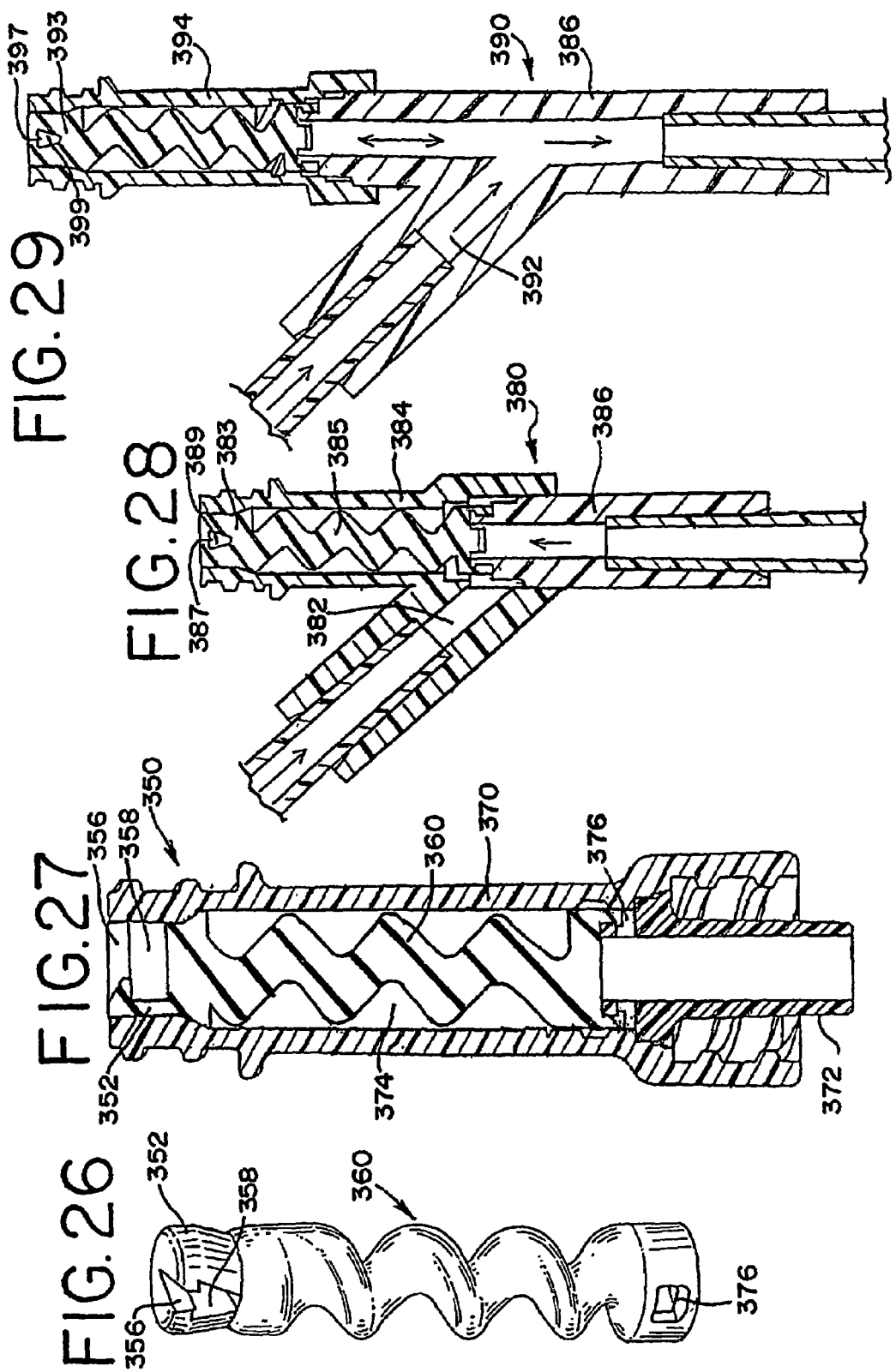

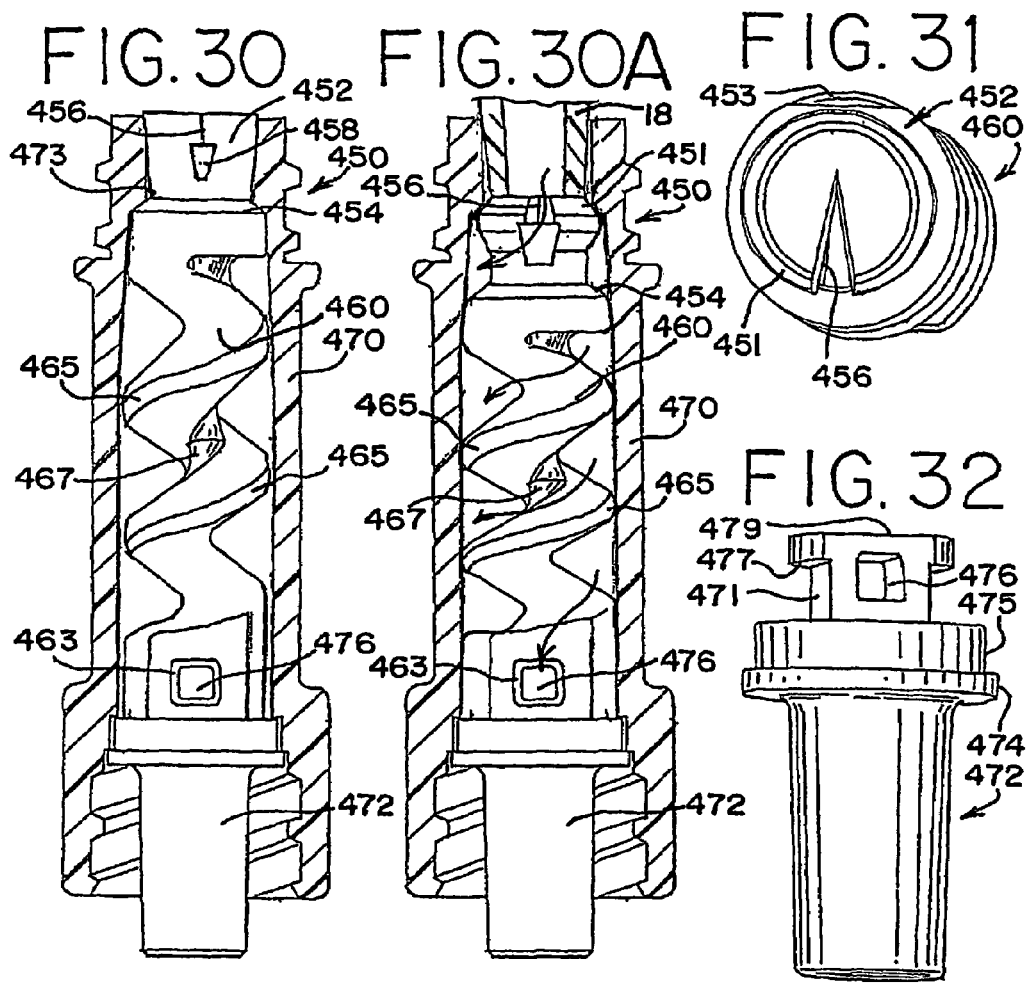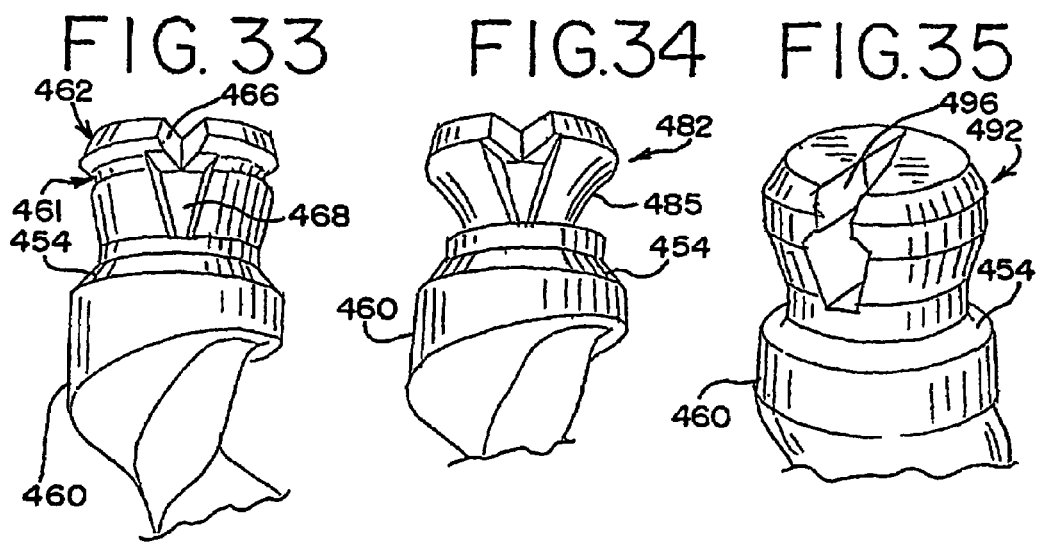

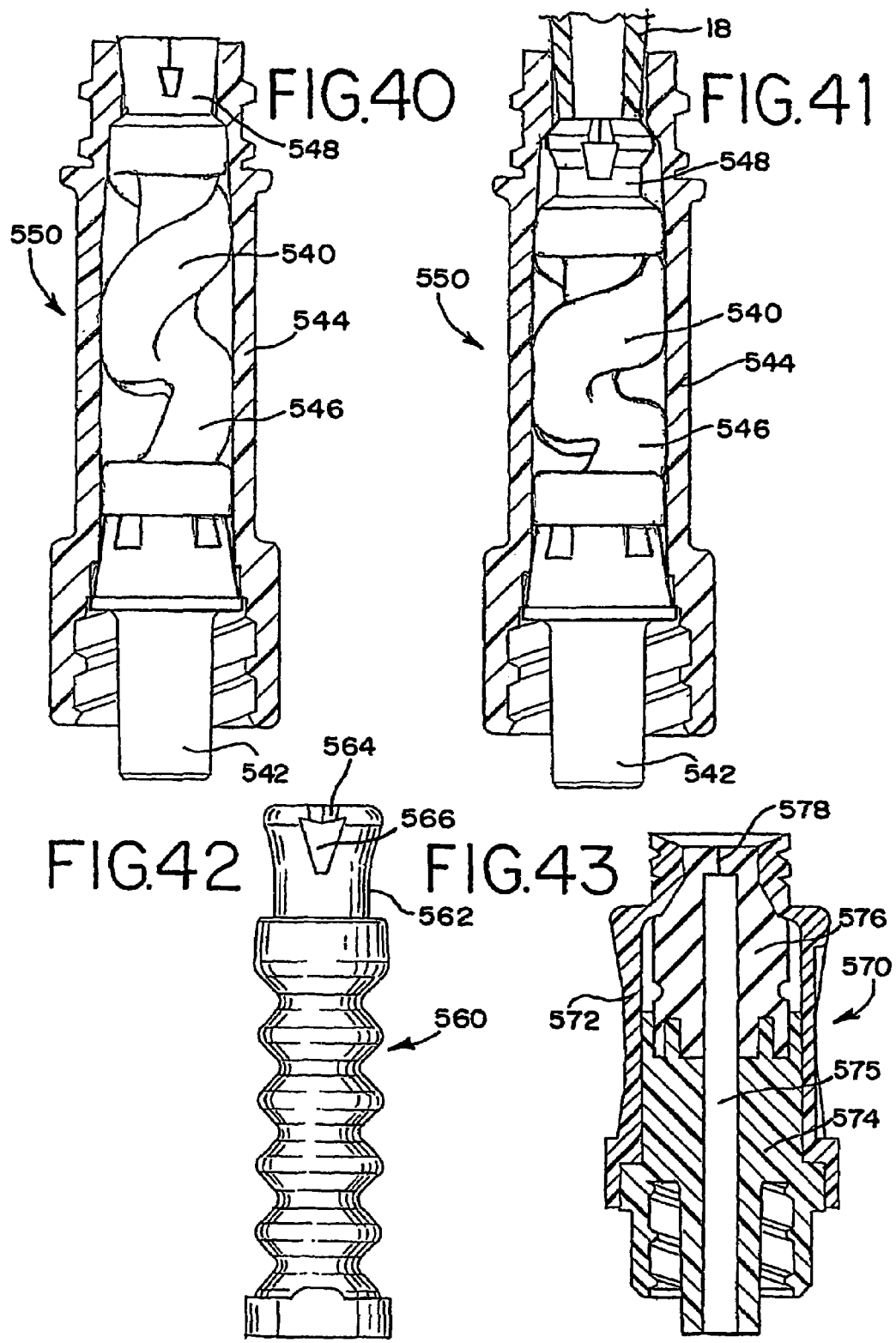

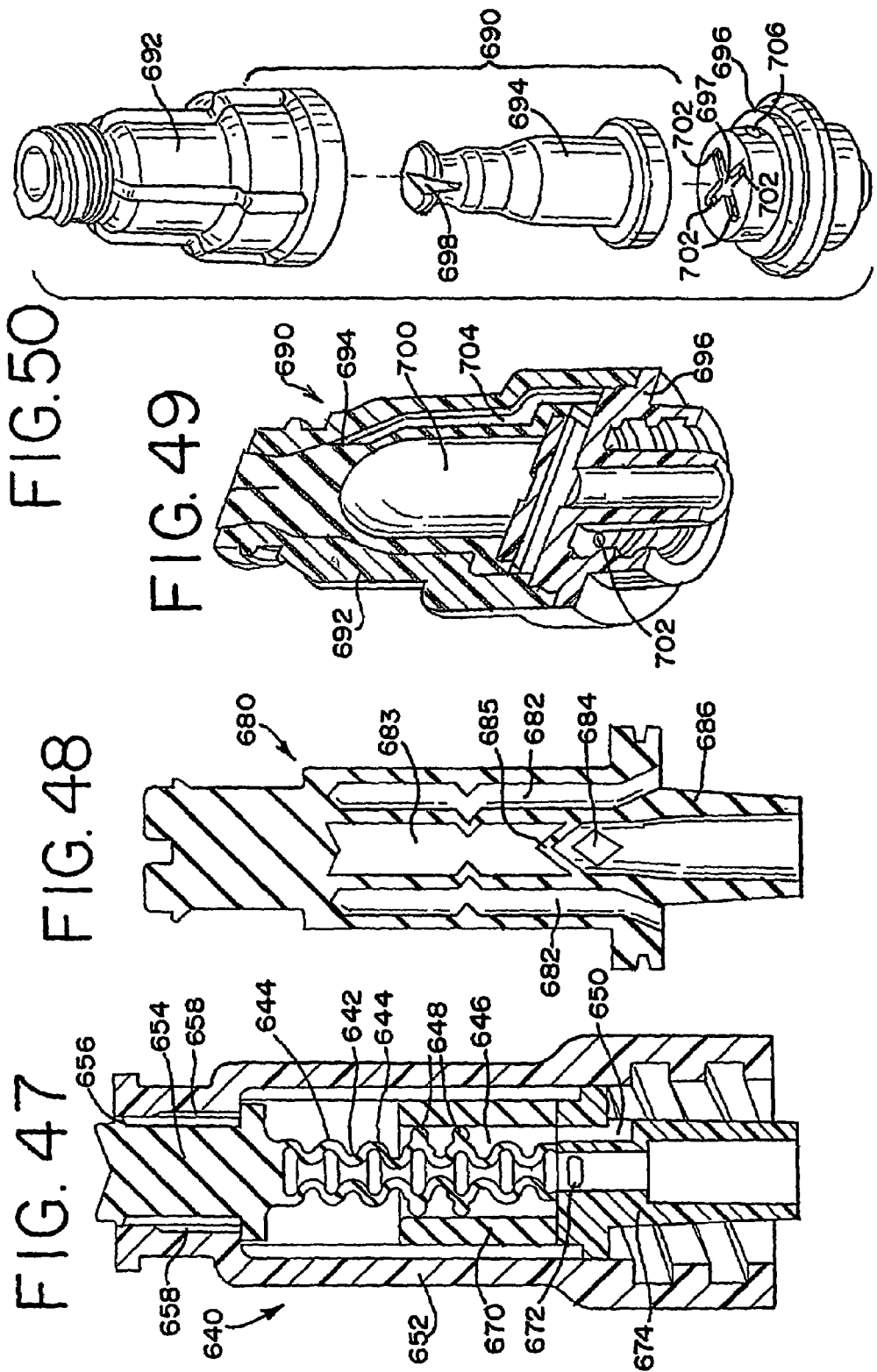

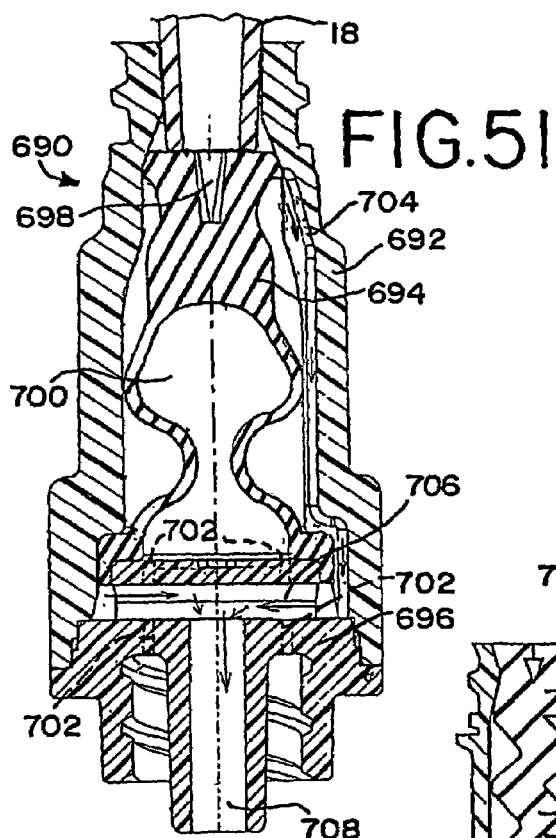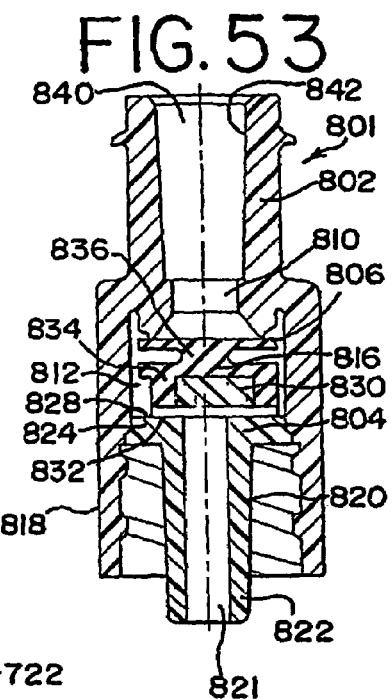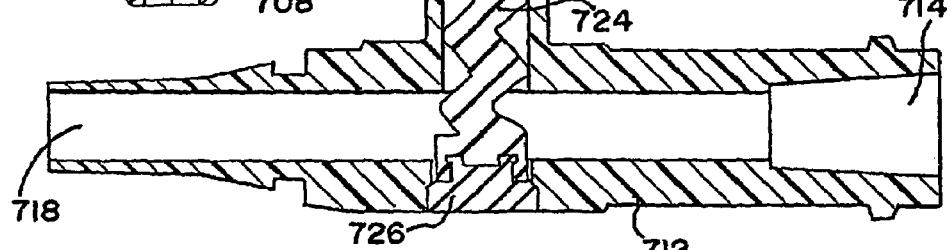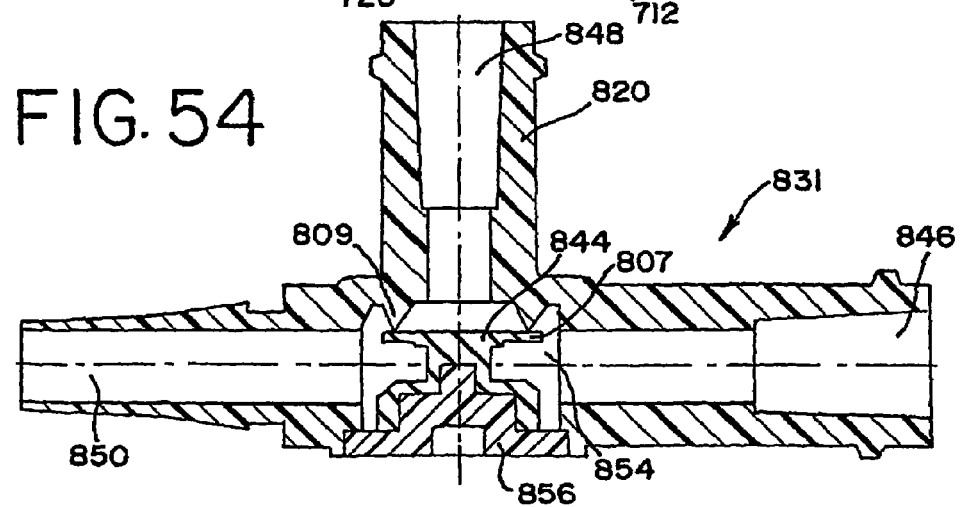

FLUID HANDLING DEVICE AND METHOD OF MAKING SAME

RELATED APPLICATIONS

The present application claims the benefit under 35 U.S.C. § 119(e) of Provisional U.S. Patent Application Ser. No. 60/479,403, filed Jun. 17, 2003; which is hereby incorporated by reference in its entirety.

BACKGROUND

This invention relates to fluid handling devices, particularly for medical purposes, and methods of making fluid handling devices. The invention is particularly suitable for needlefree access devices and check valves.

The use of hypodermic needles to inject or withdraw fluids in medical application had been standard practice up until a few years ago. Even where a patient already had an IV tubing set connected to a vein, hypodermic needles were frequently used to inject fluids into the IV tubing. Often a "Y" access device with a septum was provided in the tubing set for this very purpose. The needle was used to puncture the septum to administer the drug or other fluid, and the septum then sufficiently sealed the opening to prevent leakage, and prevent airborne bacteria from entering the system. Septums are also common on drug vials, where the needle is inserted to withdraw a quantity of the drug.

The widespread use of hypodermic needles lead to numerous needle-stick accidents. These were not only painful, but if the needle is contaminated, could cause serious disease or complications in the needle-stick victim. There has been a desire for needlefree medical systems, where a fluid can be injected or aspirated without the use of a needle, but while maintaining an aseptic leak-free system.

Numerous devices have been developed to achieve this goal. Many of those devices have been disclosed in the patent literature. One early such device is disclosed in U.S. Pat. No. 5,360,413. The different embodiments of the needleless access device disclosed in the '413 patent have proven to be influential in the design of subsequent needlefree access devices. Many of the concepts have been used in other devices. The wiper seal to seal the inlet channel against airborne bacteria and the piston head that can be easily swabbed prior to actuation are two of the more significant features.

Even with all the work and development that has transpired over the years in this area, there is still need for improvement, particularly with respect to better performance, such as greater flow rate and reduced trapped drug and fluid after flushing, and lower cost. The preferred embodiments disclosed in the '413 patent are assembled from four or five components, depending on the design. Even though the parts can be mass produced, the product cost is dependent on the number of individual components that have to be made, and then assembled. Most needlefree access devices commonly available contain at least three parts. Many prior needlefree access devices also have internal configurations that allow fluid to be trapped in the device even after flushing. Also, many prior devices are fairly large and therefore have a higher material cost and internal volume.

Check valves are also often assembled from three or more parts. For example, U.S. Pat. Nos. 5,771,935 and 4,749,003 both disclose check valves that are assembled from three separate components. The cost of such products could be reduced if they were assembled from only two parts.

The desire to reduce the number of parts that must be assembled, however, cannot override the more important fact that the fluid handling products must meet several critical design features. Thus, there is a real need for fluid handling products that can be made at a lower cost, but still meet the end user's specifications. Also, there is a need for fluid handling products that have reduced hold up-volumes, are easier to prime and flush, and that have a flow path through the device that is visible to the user so that any bubbles can be spotted and the flow of solutions can be visualized.

BRIEF SUMMARY

The present invention includes fluid handling devices, such as needlefree access devices and check valves, that are lower in cost and have low hold-up volumes. Preferred fluid handling devices may be assembled from only two parts, yet still provide at least as good, and in many ways superior, performance compared to many prior art devices. The present invention also includes check valves that may be assembled from only two parts. Methods of making fluid handling devices by a two-shot molding process have reduced labor cost and improved quality control.

In a first aspect, the invention is a fluid handling device having a housing, a sealing surface and a flow control member comprising a flexible material biased against said sealing surface, characterized in that the flow control member is overmolded onto a constructive member of the fluid handling device such that they can be handled as one unit when being assembled with the housing to produce the fluid handling device.

In a second aspect, the invention is a fluid handling device comprising a housing having an inlet and an outlet and comprising a first housing part and a second housing part; a sealing surface inside the housing; and a sealing member comprising a flexible material biased against the sealing surface; wherein the first and second housing parts are produced from thermoplastic material, and the sealing member and the second housing part are molded together such that they can be handled as one unit when being assembled with the first housing part to produce the fluid handling device.

In a third aspect, the invention is a method of making a fluid handling device comprising forming a first housing part from a thermoplastic material, the first housing part having a sealing surface; forming a second housing part from a thermoplastic material; forming a sealing member comprising a flexible material by overmolding the sealing member to the second housing part such that the second housing member and sealing member can be handled as one unit when being assembled with the first housing part; and connecting the first housing member and second housing member together, with the sealing member biased against the sealing surface, to form the fluid handling device.

In another aspect, the invention is a needlefree access device comprising a housing having an inlet and an inlet channel; and a combination outlet, biasing and piston member having a piston section moveable between a closed position in which the piston section is in the inlet channel and an open position in which the piston section is inside the housing below the inlet channel but allows fluid to flow through the inlet channel, a biasing section connected to the piston section that normally biases the piston section into the inlet channel; and an outlet section interlocked to the biasing section and having an outlet fitting in fluid communication with the inside of the housing, wherein the piston section, biasing section and outlet section are connected together such that they can be handled as one piece when assembled with the housing to make the needlefree access device.

In an additional aspect, the invention is a fluid handling device comprising a housing and a flow control member, the flow control member comprising thermoplastic material and thermosetting material overmolded to the thermoplastic material.

In a further aspect, the invention is a needlefree access device comprising: a housing and a flow control member, the flow control member comprising a thermoplastic outlet section and a resilient material overmolded onto the thermoplastic material.

In still another aspect, the invention is a flow control member for use in a needlefree access device, the flow control member comprising an outlet section formed of thermoplastic material; and a combined biasing section and piston section formed from resilient material, the biasing section being molded onto the outlet section.

In a still further aspect, the invention is a needlefree access device comprising a housing having an inlet, a base, and a main body portion having a generally cylindrical inside surface between the inlet and the base; a valve member actuatable between an open position and a closed position, wherein in the closed position the valve member prevents flow between the inlet and the outlet; a central body within the main body portion of the housing, the central body having a helical shape on its outer surface, the central body fitting against the inside of the cylindrical surface when the valve member is in its open position; the helical shape thus defining a helical flow path through the main body portion of the housing when the valve member is in an open position.

In an additional aspect, the invention is a needlefree access device comprising a housing having a round inlet, a tapered inlet channel that narrows inwardly from the inlet, a main body portion, and a base opposite the inlet; a piston member inside the housing; and a biasing member inside the housing normally biasing the piston member to close the inlet; wherein the piston member comprises a resilient material with a top having a generally elliptical shape and an opening that is closed when the top of the piston is forced into the round inlet opening but which allows flow through the opening to the outside of the piston member when the piston member is forced downwardly against the biasing force and out of the tapered inlet channel.

In a still further aspect, the invention is a method of making a needlefree access device comprising forming a housing having an inlet and a base; forming a flow control member by molding thermoplastic material to form an outlet member and molding resilient material onto the outlet member, the resilient material forming a piston section and a biasing section; inserting the flow control member into the housing such that the piston section is adjacent to the inlet; and securing the outlet member into the base of the housing.

In another aspect, the invention is a method of making a needlefree access device comprising providing a first part comprising a monolithically formed housing; providing a second part comprising a combination outlet section, biasing section and piston section; constructing the needlefree access device by securing the second part within the first part, the access device being made only from the first and second parts.

In a still further aspect, the invention is a needlefree access device comprising a housing having an inlet, an inlet channel and an outlet; and a biasing and piston member having a piston section moveable between a closed position in which the piston section is in the inlet channel and an open position in which the piston section is inside the housing below the inlet channel but allows fluid to flow through the inlet channel; and a biasing section connected to the piston section that normally biases the piston section into the inlet channel, the biasing section comprising a resilient body having a helical shape on at least part of its outer surface.

The preferred needlefree access device, being made with only two parts, can be assembled at a low cost. By using a two-shot molding process, a combination part can be made that includes several functional sections: a piston section, a biasing section and an outlet section. The unique manufacturing methods of the present invention allow this part to be made at a relatively low cost, yet the preferred needlefree access device has functional characteristics that are highly desirable. In addition, quality control is improved since only two parts have to be assembled. These and other advantages and features of the invention will be best understood in light of the attached drawings.

BRIEF DESCRIPTION OF THE DRAWINGS

FIG. 1 is a perspective view of a first embodiment of a needlefree access device of the present invention;

FIG. 2 is a view of the access device of FIG. 1 from a different perspective;

FIG. 3 is an exploded view of the combination outlet, biasing and piston member, also referred to as a flow control member, of the access device of FIG. 1;

FIG. 4 is an exploded perspective view of the access device of FIG. 1;

FIG. 5 is a longitudinal cross-sectional view of the housing used in the access device of FIG. 1;

FIG. 6 is a cross-sectional view taken along line 6-6 of FIG. 4;

FIG. 7 is a cross-sectional view taken along line 7-7 of FIG. 1;

FIG. 8 is a partial cross-sectional view taken along line 8-8 of FIG. 1;

FIG. 8A is a partial cross-sectional view of the access device of FIG. 1 shown in its open, activated position;

FIG. 9 is a perspective view of a second embodiment of combined biasing and piston sections of a flow control member of the present invention;

FIG. 10 is a cross-sectional view of a third embodiment of a needlefree access device of the present invention in its open, activated position;

FIG. 11 is a cross-sectional view of a fourth embodiment of a needlefree access device of the present invention;

FIG. 11A is a cross-sectional view taken along line 11A-11A FIG. 11;

FIG. 12 is a cross-sectional view of a fifth embodiment of a needlefree access device of the present invention;

FIG. 13 is a cross-sectional view of a sixth embodiment of a needlefree access device of the present invention;

FIG. 14 is a partial cross-sectional view of an I.V. bag using the needlefree access device of FIG. 1 as a bag port;

FIG. 15 is a cross-sectional view of a seventh embodiment of a flow control member of the present invention;

FIG. 16 is a cross-sectional view of an eighth embodiment of a flow control member of the present invention;

FIG. 17 is a cross-sectional view of a ninth embodiment of a flow control member of the present invention;

FIG. 18 is a cross-sectional view of a tenth embodiment of a flow control member of the present invention;

FIG. 19 is a cross-sectional view of an eleventh embodiment of a flow control member of the present invention;

FIG. 20 is a cross-sectional view of a twelfth embodiment of a flow control member of the present invention;

FIG. 21 is a cross-sectional view of a thirteenth embodiment of a needlefree access device of the present invention;

FIG. 22 is a cross-sectional view of the mold tool used to form the outlet section of the access device of FIG. 1;

FIG. 23 is a cross-sectional view of the mold tool used to overmold the combined biasing section and piston section of the access device of FIG. 1;

FIG. 23A is a partial enlarged cross-sectional view of an alternate embodiment of the mold tool used to overmold an alternate combined biasing section and piston section of the access device of FIG. 1;

FIG. 25 is a schematic view of a manufacturing cell that can be used to make access devices of the present invention using two vertical molding presses;

FIG. 26 is a perspective view of a fourteenth embodiment of combined biasing and piston sections of a flow control member of the present invention;

FIG. 27 is a cross-sectional view of a needlefree access device using the flow control member with the combined biasing and piston sections of FIG. 26;

FIG. 28 is a cross-sectional view of a first Y-shape needlefree access device of the present invention;

FIG. 29 is a cross-sectional view of a second Y-shape needlefree access device of the present invention;

FIG. 30 is a partial cross-sectional view of a fifteenth embodiment of a needleless access device of the present invention shown in its closed position;

FIG. 30A is a partial cross-sectional view of the needleless access device of FIG. 30 shown in its open, actuated position;

FIG. 31 is a top perspective view of the flow control member of the access device of FIG. 30;

FIG. 32 is a perspective view of the outlet member used in the access device of FIG. 30;

FIG. 33 is a perspective view of a first alternate piston section that could be used in the access device of FIG. 30;

FIG. 34 is a perspective view of a second alternate piston section that could be used in the access device of FIG. 30;

FIG. 35 is a perspective view of a third alternate piston section that could be used in the access device of FIG. 30;

FIG. 40 is a cross-sectional view of the access device of FIG. 38 shown in its closed position;

FIG. 41 is a cross-sectional view of the access device of FIG. 38 shown in its open, activated position;

FIG. 42 is an elevational view of an nineteenth embodiment of combined biasing and piston sections of a flow control member of the present invention;

FIG. 43 is a cross-sectional view of a twentieth embodiment of a needleless access device of the present invention shown in its closed position;

FIG. 47 is a cross-sectional view of a twenty-first embodiment of a needleless access device with positive displacement of the present invention shown in its closed position;

FIG. 48 is a cross-sectional view of a twenty-second embodiment of a flow control member used to make a positive displacement needleless access device of the present invention;

FIG. 49 is a perspective, cross-sectional view of a twenty-third embodiment of a needleless access device with positive displacement of the present invention shown in its closed position;

FIG. 50 is an exploded view of the access device of FIG. 49;

FIG. 51 is a cross-sectional view of the access device of FIG. 49 in its open, activated position;

FIG. 52 is a cross-sectional view of a twenty-fourth embodiment of a needleless access device of the present invention shown in its closed position;

FIG. 53 is a cross-sectional view of a first embodiment of a check valve of the present invention; and FIG. 54 is a cross-sectional view of a second embodiment of a check valve of the present invention.

DETAILED DESCRIPTION OF THE DRAWINGS AND THE PRESENTLY PREFERRED EMBODIMENTS

Figure 24:
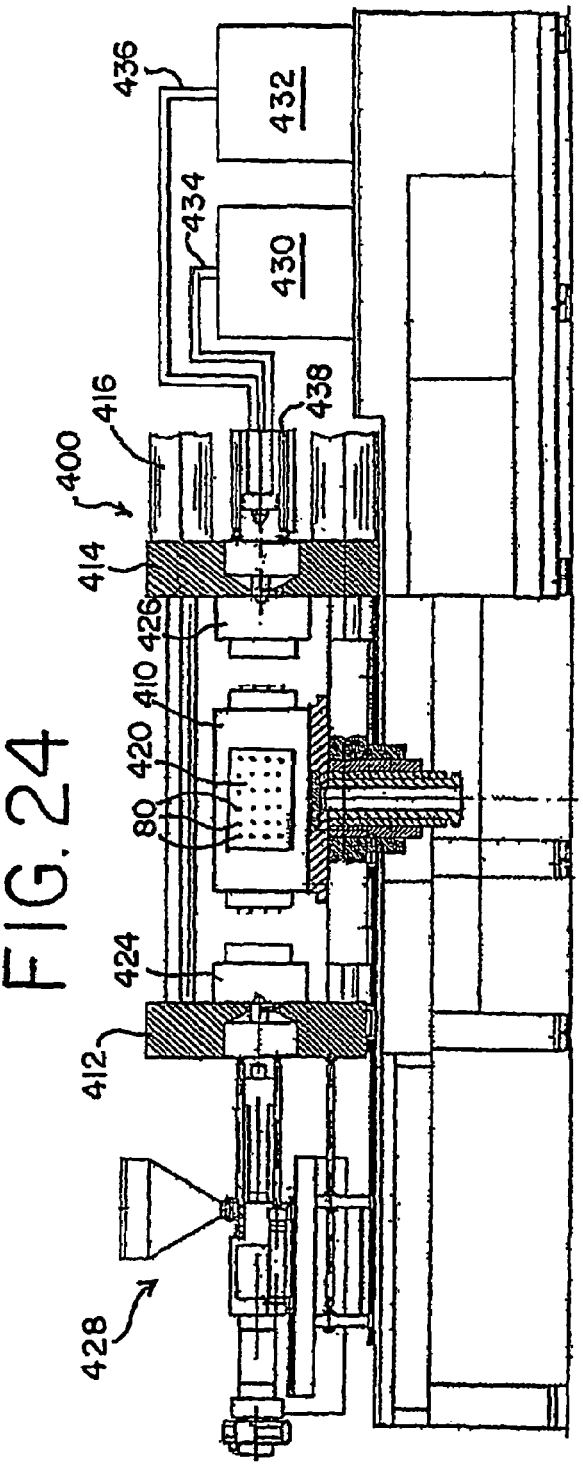
FIG. 24 is an elevational schematic view of a horizontal molding press that can be used to make needlefree access devices of the present invention.

As used herein, the term "fluid handling device" means a device that allows a fluid, particularly a medical fluid, to be transferred from one location, through the device, to another location. The fluids can be saline solutions, solutions containing drugs or other medicaments, or biological fluids, including blood. The fluids can be gases, especially gases used for medical purposes.

One class of fluid handling devices are needlefree access devices, such as luer activated valves that allow a syringe tip to be inserted into the access device and open the valve so that a fluid can be administered or withdrawn through the access device without a hypodermic needle. Many other needlefree access devices are parts to IV administration systems. Of course there are needlefree access devices that will not necessarily include valves, nor need to mate with standard luer access devices. Many other fluid handling devices, such as bag ports, vial adapters, stopcocks, manifolds and the like, may be equipped with needleless luer activated valves. Another class of fluid handling devices to which the present invention especially pertains is check valves.

The first preferred embodiment of a needlefree access device 10 of the present invention is shown in FIGS. 1-9. As noted above, the access device 10 is assembled from a first part, which comprises a housing 20, and a second part 40, which comprises a combination outlet, biasing and piston member. This second part acts as a flow control member. Together the two parts 20 and 40 form the complete needlefree access device 10. As will be explained in detail, the flow control member 40 provides several functional parts to the access device 10. It is preferably made in a two shot molding process. Since one molding press is needed for the two shot molding, the cost for this part is less than if it were made from two separate molding operations. Furthermore, since the access device 10 is made from only these two parts, it can be assembled at a lower cost than if it were assembled from three or more parts.

The housing 20 is preferably monolithically formed, such as by an injection molding process. As best seen in FIGS. 4 and 5, the housing has a round inlet 22 leading into a tapered inlet channel 24 that narrows inwardly from the inlet 22. The inlet 22 and inlet channel 24 preferably form a female luer taper for engaging with a syringe tip 18 (FIG. 9) having a standard male luer taper. The housing also includes a base 26 with threads 36 for forming a luer lock.

The housing 20 has a main body portion 28 with a generally smooth cylindrical inside wall surface 29 between the inlet 22 and the base 26. The housing also includes an internal sealing surface 30. The outside of the upper portion 32 of the housing 20 also includes threads 38 for a luer lock.

The combination outlet, biasing and piston member 40 can be thought of as having three sections: a piston section or head 50, a biasing section 60 and an outlet section 70. The piston section 50 provides a piston member with a wiper seal 52 and a sealing member, also referred to as a valve member 54. The piston section is movable between a closed position, in which the piston section is in the inlet channel 24 (FIG. 8), and an open position, in which the piston section is inside the housing below the inlet channel, but allows fluid to flow through the inlet channel (FIG. 8A). The wiper seal 52 is dimensioned so that it ensures sealing in the inlet channel acting to maintain sterility against bacterial contamination when the piston section is in its closed position, and to wipe the inlet channel so as to leave the wiped area in a clean state. In the closed position, the valve member 54 of the piston section seals against the internal sealing surface 30 of the housing, thus preventing flow between the inlet and the outlet. This is primarily used to prevent backflow through the access device when the piston section is in the closed position. The biasing section preferably provides sufficient force to keep the valve member 54 closed even if a vacuum is drawn on the outlet.

The biasing section 60 is connected to the piston section 50 and normally biases the piston section into the inlet channel 24. The biasing section 60 has a central hollow portion 62 (FIG. 6), which allows the wall 64 of the biasing section 60 to collapse. The biasing section 60 also provides a central body having a helical shape on its outer surface, such as a helical groove 64 on the outside thereof. Otherwise, in a collapsed state, the central body fits against the inside of the cylindrical surface 29 of the housing. The helical groove 64 thus defines a helical flow path or channel through the main body portion 28 of the housing 20. When the access device is in its open position (FIG. 8A) the helical flow channel formed in the outer surface of the biasing section 60, around its center portion, preferably has a cross-sectional width 66 of about 0.02 inches. Preferably the biasing section 60 and piston section 50 are formed as one monolithic piece.

The outlet section 70 is connected to the biasing section 60, preferably by having the biasing section 60 overmolded to the outlet section. The outlet section provides an outlet fitting 72, preferably having a male luer taper. The outlet fitting 72 is in fluid communication with the inside of the housing. The outlet section includes a flange 74 that fits in a recess 37 in the housing 20 (FIG. 5). Thus, the outlet section 70 forms a closure to the housing 20, thus directing flow through the housing to pass through the outlet fitting 72. Fluid can enter the outlet fitting through openings 76 formed near the top of the outlet section. These openings are in fluid communication with the central flow channel 78 through the center of the outlet section 70. Preferably the housing 20 includes an internally threaded section 35 (FIG. 5) adjacent the connection between the biasing section and the outlet section so that fluid traveling down the helical flow channel 64 can make it past the connection between the biasing section and the outlet section and into openings 76.

The biasing section and piston section are preferable made of resilient material, and more preferably a resilient thermosetting material such as silicone, whereas the outlet section is preferably made of rigid thermoplastic. In the past, these two materials have not been commonly molded together, especially in a configuration wherein the thermosetting material is formed in a shape that for the most part extends away from the thermoplastic component in a free-standing manner. (U.S. Pat. No. 4,983,344 discloses an electrical connector where the outer body member is made of thermoplastic and is filled with a thermosetting material, but in that connector, the thermosetting material is mostly within the thermoplastic body, extending only slightly outside of the thermoplastic body and only on one end.) Silicone does not generally adhere to thermoplastic. However, a thermosetting material is desirable for the biasing section 60 because it needs to be resilient, and, more importantly, not "cold flow". Most thermoplastics, including thermoplastic elastomers, experience cold flow, meaning that they permanently deform when left under pressure. If the biasing section were made of a material that experienced cold flow, after a period of storage in an assembled state, the biasing member would no longer continue to urge the piston section 50, and valve member 54 in particular, into the inlet channel and against the sealing surface 30.

The wiper seal 52 also should maintain its shape over time. Thermoplastic elastomers that are currently commercially available would provide the resiliency needed, but would undergo cold flow if the needlefree access device 10 were assembled and placed in storage awaiting distribution and use. However, in the future thermoplastic elastomers may be developed which would not have a detrimental degree of cold flow.

The top of the preferred piston is either flush with, or more preferably, extends out of the inlet 22 of the housing so that it can be aseptically swabbed. The piston section 50 of the preferred embodiment also provides a unique inlet flow path that is made possible because a resilient material is used. The top of the piston section has a generally elliptical shape in its unconfined form and a wedged shaped opening 56 that is closed when the top of the piston section 50 is forced into the round inlet opening. When the piston member is forced downwardly against the biasing force and out of the tapered inlet channel, the normally generally elliptically top portion with wedged shaped opening 56 returns to its underformed shape as the syring tip forces it down out of the inlet channel to a point in the housing having a wider cross section. The opening 56 extends radially from the longitudinal centerline of the piston member. However, the opening 56 does not interconnect with the hollow central portion 62 of the biasing section. Thus, when the access device is accuated, the flow out of the syring tip passes through the opening 56 and out to the side of the piston member into an area of reduced diameter above the valve member 54 portion of the piston section 50. From here it can pass down the helical flow channel 64, through the openings 76 and out the central flow channel 78.

Rather than have a wedge shaped opening 56, other opening shapes may be used. A V-shaped groove extending across the minor axis of the elliptical shape of the piston top will have the same ability to close up when forced upwardly into the inlet channel, but spring back open when depressed, and allow fluid flow out both sides of the groove. Such a V-shaped groove is shown in the embodiments of FIGS. 15-17.

As noted above, the access device 10 is preferably made by providing a first part comprising the monolithically formed housing 20, providing a second part comprising the combination outlet section, biasing section and piston section, and constructing the needlefree access device 10 by securing the second part within the first part. Preferably the housing 20 is made of a thermoplastic material that allows the flange 74 on the outlet section to be sonically welded into the recess 37 in the base of the housing 20. In this manner the access device can be assembled from only two parts. Thus, in the preferred embodiment of the invention, piston section 50, biasing section 60 and outlet section 70 are connected together such that they can be handled as one piece when assembled with the housing 20 to make the needlefree access device 10. Hence, the combination outlet, biasing and piston member exists as a single part before the needlefree access device is assembled.

The preferred combination outlet, biasing and piston member 40, which constitutes one variety of a flow control member, is made by first injection molding thermoplastic material to form the outlet section 70. FIG. 22 shows a mold that can be used for this purpose. The mold has a base section 80 and a first top section 82. The central flow channel 78 is formed by a center core pin 84. The core pin 84 has an extension making it longer than needed, as will be explained later. The openings 76 are formed by side action pins 86, as is well known in the art of thermoplastic molding. Hot, molten thermoplastic material is injected through port 88 to form the outlet section 70. After the outlet section 70 has solidified, the first top mold section 82 is removed. However, the outlet section is not ejected from the mold base 80, nor is the center core pin 84 removed. Instead, a second top section mold is put in place, as shown in FIG. 23. This second top mold section is made of two halves, 90 and 92. Each mold half has an extension 94 that extends into one of the openings 76 to keep it open during the subsequent overmolding operation. Mold half 90 includes a port 96 through which resilient material is injected into the cavity. Mold half 92 includes a protrusion 98 that is used to form the wedge shaped opening 56 in the piston section 50. The extended part of the center core pin 84 now forms the hollow central portion of the biasing section 60. The helical flow channel is made by flights on the insides of the top mold halves (either chemically or by solidifying from a molten state) 90 and 92.

In the preferred embodiment, the outlet section 70 interlocks with the biasing section 60. This can be either a chemical or physical interlocking. If the resilient material does not bond to the thermoplastic material, the junction between the outlet section 70 and biasing section 60 can be designed so that the biasing section is mechanically interlocked to the outlet section 70. This is most easily done by forming an undercut in the top of the outlet section 70 just above the openings 76, as shown in FIG. 23A. However, first top mold 82 may then need to be made of two parts. It is important that mold base 80 be made of only one part so that there is no part line in the luer taper section 72 of the outlet section 70.

As used herein and in the claims, the term "overmolding" is used to refer to a process in which a first part is placed in a mold tool such that at least a portion of the surface of that part is exposed within the cavity of the mold tool. Thereafter material is introduced into the cavity to form an overmolded part having the shape of the cavity. The new material is in intimate contact with the exposed surface of the first part within the cavity, and is thus overmolded onto the first part. The first part may be of a different or the same material as used to make the overmolded part. The overmold material may form a chemical or melt bond to the first part, but this is not always the case. As just discussed, the overmolded biasing section 60 may be mechanically interlocked to the outlet section 70.

In the preferred embodiment of the invention, the outlet section 70 is not removed from the mold base 80 until it has the biasing section 60 and piston section 50 connected to it. In this manner the combination part can be handled as one piece during the assembly process. This simplifies the assembly, and hence reduces the cost of the needlefree access device 10. In addition to overmolding, there are other ways to produce such a connected part using in-press assembly, meaning assembly of the combined part while still in the molding press. For example, the biasing and piston section could be molded with a different mold that did not have the outlet section already in it. Both the outlet section still in its base mold and the combined biasing and piston section still held by its mold could be brought together and joined, such as with an interference fit between the parts. The parts only need to be secured together to the extent that they remain together until inserted into a housing. The joint between the biasing section and outlet section need not prevent leakage because any leakage would be inside the housing and flow into the same path that fluid will flow anyway.

The outlet section 70 will typically be molded from a thermoplastic injected at a temperature of between about 300° F. and about 800° F., and at a pressure of between about 500 psi and about 2000 psi. The mold base 80 will typically be cooled so as to maintain a temperature of between about 50° F. and about 300° F. when the thermoplastic material is injected. The precise temperatures and pressures will depend on the mold configuration and the thermoplastic used, as is well known in the art. The thermoplastic material will most likely be selected from the group consisting of polycarbonates, polysulfones, nylons and acrylics. When polysulfones are used, the injection temperature will typically be in the 700-800° F. range. Polycarbonates, which are presently preferred, are injected at a temperature of about 600° F. A particularly preferred thermoplastic is Lexan™ polycarbonate from GE Plastics.

The second top section mold halves 90 and 92 will typically be heated so as to cause the thermosetting material to cure. The themosetting material is preferably silicone rubber, which is made by mixing a silicone part A with a silicone part B. This mixing will most typically occur just before the material is injected into the cavity of the second top section mold. However, the materials may be premixed and stored until used as long as it is stored under conditions and for a duration that do not cause it to solidify. The material will typically be injected at a pressure of between about 100 psi and about 900 psi, and at a temperature of between about 50° F. and about 100° F. The second top mold section will preferably be heated to a temperature of between about 250° F. and about 400° F. when the mixture is injected. A preferred material is LIM607 from GE Silicone, a 70 durometer liquid injection moldable material.

A simple manufacturing cell 300 that could be used to mold the flow control member 40 on pilot scale is shown in FIG. 25. The cell has two molding press stations 302 and 304, a holding station 306, and an off-loading station 308. Several multicavity mold bases 310, 312 and 314 are used, each identical and containing eight cavities of a design of the mold base section 80. At molding press station 302, thermoplastic is injected into the cavities of mold base 310 to form eight separate outlet sections 70. The mold top held in press station 302 has eight cavities of the top section 82. At the same time this operation occurs, mold base 312, which was previously in molding press section 302 and had the outlet sections 70 molded in it, is in molding press section 304, where thermosetting material is injected to form the biasing section 60 and piston section 50. Of course molding press section 304 carries an eight cavity mold, each with the mold halves 90 and 92 operational therein. At the same time that the two molding operations are going on in molding press stations 302 and 304, finished flow control members 40 are off-loaded at off-loading station 308 from mold base 314 which previously went through both molding press sections 302 and 304.

At the end of one cycle, when molding press sections 302 and 304 are open, the mold bases 310, 312 and 314 are moved in a counter clock-wise direction. Mold base 310 is first moved to holding station 306. Mold base 314 now empty, is moved from the off-loading station 308 to the first molding press section 302. Mold base 312 is moved from molding press section 304 to off-loading station 308. Then mold base 310 can be moved from holding station 306 into the molding press section 304. The molding and off-loading operations are then repeated, and the cycle continues. One operator stationed at position 316 moves the mold bases 310, 312 and 314 to their next location, while a second operator at position 318 off-loads the molded parts.

A preferred high-capacity manufacturing operation that may be used to mold the flow control member 40 uses a rotary turntable molding press 400, such as a Krauss Maffei brand rotary press, modified to use liquid inject moldable material on one side, as shown in FIG. 24. The press 400 has a rotating center section 410, a left platen 412 used to mold thermoplastic material and a right platen 414 used to mold thermosetting material. Platen 414 stays fixed, but center section 410 and left platen 412 are moveable along linear guiding rails on the machine bed. Double acting hydraulic cylinders 416 or other types of mechanical devices reciprocate to move the platen 412 and center section 410 from an open position as shown to a closed position in which the moveable portions are shifted to the right to close up the molds carried on the platens and center section 410. These cylinders also supply the needed clamp pressure for the injection molding operations. The center section 410 can be designed to carry either two or four multicavity mold bases 420, each cavity having the shape of mold base section 80 without injection port 88. Platen 412 carries the first mold top 424 with cavities of the shape of top section 82, modified to include a port to inject the thermoplastic. Platen 414 carries the second mold top 426 with cavities in the shape of mold halves 90 and 92. The center section 410 slides on a bed, and has means (not shown) to slide it back to the center position after a molding step.

A thermoplastic injection system 428 is connected to and travels with platen 412, so as to be able to inject molten thermoplastic through hot runners in the mold top 424. The thermoplastic injection system 428 is conventional in design, with a heated barrel and a screw with flights to create the necessary injection pressure. On the right, stationary side, the press 400 holds two tanks 430 and 432 which hold the two silicone part A and silicone part B, respectively. Metering pumps draw the liquid from the tanks and feed it through hoses 434 and 436 into a screw cylinder 438 where the two liquids are mixed. The screw cylinder also builds the pressure to inject the silicone through runners in a cold plate formed as part of second mold top 426. However, the rest of the mold top 426 is heated to provide conditions that will cure the silicone once it is mixed and injected.

The center section 410 includes energy circuits that allow the mold bases 420 to be cooled. For example, the mold bases may be left at about 40-60° F. The energy circuits also actuate moveable portions within the mold bases 420. Water is also used to cool the first mold top 424, to keep it at a temperature of about 100-130° F. The second mold top 426 is held a temperature of about 350-375° F.

The center section 410 includes a rotary table, to allow the center section to rotate between its various positions. If four mold bases 420 are used, as shown in FIG. 24A, the mold bases rotates 90° at each step between a first molding station, where the thermoplastic is injected to form outlet sections 70, to a cooling station, to the second molding station where the silicone is overmolded, and finally to the off-loading station where the finished parts are ejected from the mold base 420.

Figure 24C:
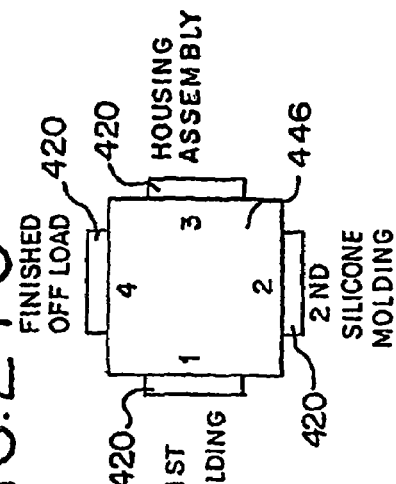
FIG. 24C is a schematic top view of a third embodiment of the operation of the central portion of the press of FIG. 24.
Figure 24B:
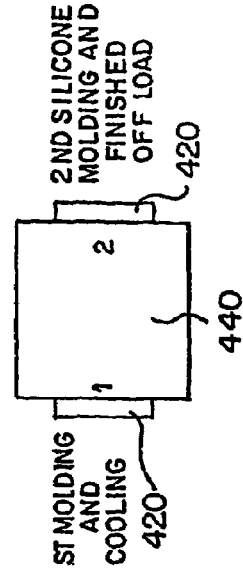
FIG. 24B is a schematic top view of a second embodiment of the operation of the central portion of the press of FIG. 24.
Figure 24A:
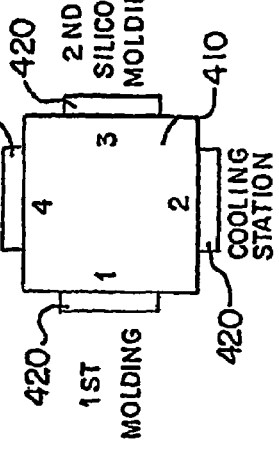
FIG. 24A is a schematic top view of one embodiment of the operation of the central portion of the press of FIG. 24.

Alternatively, in the embodiment shown in FIG. 24A, the cooling station could also include a thermoplastic treatment station, such as a plasma treatment operation, which may be used to improve the adherence of the resilient thermosetting material to the thermoplastic material of the outlet section.

FIG. 24B shows another alternative arrangement where only two mold bases 420 are in place on center section 440. In this embodiment, the first molding and cooling operations both occur while the first mold base 420 is in the first station. Meanwhile, the second molding with silicone, followed by off-loading, is occurring with the second mold base 420 in the second position. The center section 440 is rotated 180° between each operation.

FIG. 24C shows yet another embodiment where all four molding stations are used on center section 446. In this embodiment, the silicon is molded onto the outlet section to form the flow control member at the second station. At the third station, the housing is assembled to the flow control member while it is still held in the mold base 420. This in-mold assembly requires the housings to be brought to the third mold station in a way that they can be assembled in an automated fashion with the flow control members. This may be done by leaving the housings in the mold base in which they were formed and bring the entire mold base and housings to the third station, preferably with a robot arm. Of course the spacing of the housings in their mold base would have to match the spacing of the outlet sections in the mold base 420 for this to work. Finally in the fourth station the entire needleless access device is off-loaded.

A press assembly with more than four stations could also be used if additional steps, such as both cooling and plasma treating, and in-mold assembly with the housings, were all to be accomplished.

The needlefree access device of the present invention may be made with different parts than those shown in FIGS. 1-8. For example, combined biasing and piston sections for a second embodiment of a flow control member are shown in FIG. 9. The biasing section 91 differs from biasing section 60 in several respects, most significantly in that it is not hollow. Rather, the biasing section 91 has a solid central portion with a helical shape on its outer surface. However, the central portion is reduced in its average outside diameter so that the cross-sectional area of solid resilient material is comparable to the cross-section of material in the biasing section 60 so that the biasing section 91 can still collapse. The helical shape of its surface has a steeper pitch than in biasing section 60. However, it cooperates with a housing (not shown) to define a helical flow path 95 when the valve member is open. The piston section 93 uses the same wedge shaped opening 97 as is used in piston section 50. The combined biasing section 91 and piston section 93 are preferably formed as one monolithic part, overmolded onto an outlet section (not shown) that may have the same configuration as outlet section 70. They are then inserted as a combined outlet, biasing and piston member into the housing just as with the access device 10. A syringe tip can be pushed down to compress the biasing member 91 just as in FIG. 8A. The wedge shaped opening 97, which is closed when the piston 93 is in a round inlet of a housing, then opens up to allow fluid to travel downwardly into the housing and out of opening 99.

A third embodiment of a needlefree access device 100 is shown in FIG. 10. The needlefree access device 100 is also constructed from two parts. A housing 102 has a shape very similar to housing 20 of needlefree access device 10, and the flow control member 104 is very similar to the flow control member 40. The primary difference is the shape of the opening 106 in the piston section. Whereas opening 56 was wedge shape, the opening 106 is more of a "U" shape that extends across the small diameter of the elliptical head. The opening 106 is closed when the biasing section forces the piston section into the inlet channel of the housing 102. However, as shown in FIG. 10, when a syringe tip 18 is inserted and depresses the top of the piston, the resiliency of the piston causes the opening 106 to open up so that fluid can flow from the syringe tip and out through the side of the piston section and follow a helical flow path around the biasing section as in access device 10.

Just as with flow control member 40, the flow control member 104 has a thermoplastic outlet section 108 with thermosetting material, such as silicone, overmolded to it to form the biasing section and piston section.

A fourth embodiment of a needlefree access device 130 is shown in FIGS. 11 and 11A. The housing 132 used in this access device is similar to housing 102, but includes a horizontal sealing surface 133. The piston section 138 and the biasing section 140 both include openings 142 formed sideways through the resilient material. These allow the biasing section 140 to be compressed by a syringe tip forcing the piston section 138 downwardly. In the embodiment of FIG. 11, the flow path is around the outside of the biasing section as with the previously described embodiments. However, the flow path does not have a helical shape. Rather flow channels 143 are formed in the side walls 144 of the housing 132. These flow channels connect to a circumferential flow channel 145. Openings 146 are formed in the outlet section 148, similar to openings 76 in outlet section 70. The openings 146 are adjacent to and in fluid communication with circumferential flow channel 145. Another feature of needlefree access device 130 is that it creates positive displacement when activated. In the embodiment of FIG. 11, the outlet section 148 must be molded from a resilient thermoplastic in order for the portion of the mold tool that create voids 149 to be withdrawn after the outlet section is molded. In any event, again, the part can be made by a two shot molding process like the other embodiments. The voids 149 are open to the atmosphere out the bottom of the access device. Thus, air can be forced out the bottom when the device is activated and flow back when the piston section returns to its position shown in FIG. 11. In this manner, the closing of the piston does not draw fluid back up the outlet section 148 when valve closes.

As shown in FIG. 11A, the outlet section 148 is tied to the material 141 surrounding voids 149 by webs 147. The openings 146 extend through the webs 147 to provide fluid communication between the interior of the housing 132, including channels 143 and 145, and the center flow path in outlet section 148.

The needlefree access device 150 shown in FIG. 12 is much like the access device 130 except that the flow path through the body of the access device is through a helical groove 154 made in the side wall of housing 152, rather than the longitudinal flow paths 143 shown in FIG. 11. The top section of housing 152 also includes some helical vents 157. These vents do not extend all the way to the top of the housing. However, they do extend to the shoulder that is used to make the sealing surface inside the housing. The vents allow the piston section to close most of the way without the wiper seal causing reflux. The vents are smaller in their outer diameter than the top of the biasing section so that the main seal can still be made.

The access device 170 shown in FIG. 13 is somewhat different in that the biasing section 175 is molded as if it were two zigzag members 177 and 178. Each is as thick as half the diameter, and as wide as the diameter, of the inside of the housing. The mold tool that forms this part has matting surfaces that contact each other over most of the longitudinal plane through a diameter of the access device. However, each of these tool surfaces has a zigzag pattern cut into it, but the zigzags are opposite to one another. Thus when the tool closes up, the corner portions of the cuts are opposite flat steel, while the central sections of the cuts intersect with one another. The resulting molded biasing section thus has central areas in which the two zigzag pieces connect to one another. This design has a flow path that goes back and forth across the width of the housing, through the spaces in between the members 177 and 178, as it flows downwardly. Also, longitudinal flow path channels 184 and circumferential flow channel 183 are provided in the side wall of the housing 186 so that fluid can flow into an opening 180 formed in the outlet section 182. Again, this part can be molded in a two shot molding process, where the outlet section 182 is molded first and the piston section and biasing section 175 are overmolded onto it. FIG. 13 shows a mechanical lock between the thermosetting material used to make the biasing section 175 and the thermoplastic used to make the outlet section 182.

FIG. 14 shows how the needlefree access device of the present invention can be used as a bag port on an IV bag 200. The access device 210 has nearly the same configuration as access device 10, except that the base of the housing and outlet section are modified because they are sealed into the IV bag and do not need to be connected to an IV line. As with other IV bags, a membrane seal 206 is provided on the bag, which may be punctured with a spike 207. The bag can thus be stored for a long time in a sterile condition until it is punctured. The spike is sized to form an interference fit with the walls 208 of the port initially sealed by membrane 206. The spike is then used to withdraw fluid from the IV bag. The access device 210 provides a port where a drug can be injected into the fluid within the bag 210.

The access device 210 can also be used in a large volume drug container which may be in the form of a bag that may contain hundreds of doses of drug. The needlefree access device 210 is then used as an access port to withdraw a single dose from the large volume container. The access device 210 may also be used as an access port on a diluent container, such as a bag that contains a saline solution.

In this regard, it should be appreciated that other embodiments of the access devices of the present invention could also be used as an IV bag port. It should also be noted that the needleless access device of the present invention can be used for other purposes, such as a vial adapter, to allow fluid to be aspirated from a vial without the use of a needle. Of course the internal components of the access device can also be used to make Y shaped access devices (see FIGS. 28 and 29) by using a housing having another inlet.

A variety of flow control members that can be used to make other embodiments of needlefree access devices of the present invention are shown in FIGS. 15-20. These flow control members can be assembled with a housing such as housing 20 to make a needlefree access device, or can be used to make y-site needlefree access devices.

The flow control member 240 shown in FIG. 15 differs from flow control member 40 in three main ways. First, the opening 246 in piston section 242 is V shaped, as opposed to wedge shaped. Second, the outside of the biasing section 244 has a pointed configuration in the flights of the helical path. Third, the inside surface of the hollow portion 248 is not smooth, but rather also has a helical groove in it. This is thought to help the biasing section deform more uniformly when depressed. The center core pin used to make the hollow portion 248 will still be able to be withdrawn because of the resiliency of the material used to make biasing section 244. Alternatively, it can be twisted out to follow the geometry of the internal helix.

Flow control member 250, shown in FIG. 16, is similar to flow control member 240, except the outside of biasing section 254 does not have a pointed configuration. However, it still provides a helical flow path.

Flow control member 260, shown in FIG. 17, has a thin-walled biasing section 264, with a helical pattern both on the inside and outside, such that the thickness of the wall of the biasing section is generally uniform.

FIG. 18 shows a flow control member 270 that is different in that it has a flow path through the piston section. An opening 276 in the piston section 272 interconnects with the central hollow section 278 in the biasing section 274. The piston section 272 may have an elliptical top section, with the opening 276 being closed until the piston section 272 is depressed to a point within a housing having a larger diameter, at which point it can open so that flow can go through the piston section.

Flow control member 280, shown in FIG. 19, is similar to flow control member 270 in having an opening 286 providing a flow path through the piston 282. However, the hollow central section 288 is formed in an undulating pattern to match the outside of the biasing section 284, thus creating a "bellows" design that can collapse as the piston 282 is depressed.

FIG. 20 shows another embodiment of a flow control member 290 that is designed to collapse in a different manner since the biasing section 294 has holes axially through its center, as well as recesses 298 in its sides. The piston section 292 can have a wedge shaped opening, or the entire piston section can cock to one side as it is depressed and the biasing section buckles unevenly. In either event, the flow of fluid then goes around the outside of biasing section 294 until it can enter openings 297. The housing used with flow control member 290 will preferably have an internal threaded section such as section 35 in access device 10 (FIG. 5).

Another two shot flow control member with quite a different design is used in needlefree access device 320 shown in FIG. 21. In this embodiment, the biasing section and piston section are combined in a single preslit septum valve 324. The housing 330 has a top section 331 that includes an annular ridge 332.

An inlet member 340 includes outside threads 344 to form a luer lock, and an inside shape that allows it to fit against the annular ridge 332. The inlet member 340 also includes an internal flange 346 to help secure the valve 324 to the inlet member 340. The inlet member 340 is molded first out of a thermoplastic material. The preslit septum valve 324 is overmolded inside of the inlet member, using a resilient material. The valve 324 has a slit 326 made in it either as part of the molding operation or afterwards. The combined pre-slit septum valve and inlet member is then sonically welded to the top 331 of the housing 330 to make the access device 320. The inlet member 340 preferably has a luer taper surface on its inside, which allows for a luer slip connection with a syringe tip. When the syringe tip is inserted into access device 320, the septum opens and the valve deforms inwardly, but is prevented from coming apart from the inlet member 340 because section 328 is captured between the inlet member 340 and the top 331 of the housing 330.

Another embodiment of a needlefree access device 350 is shown in FIGS. 26 and 27. This access device 350 uses a flow control member with a biasing section 360 which is solid in its center section and has a helical shape, much like the combined biasing and piston sections shown in FIG. 9. The housing 370 can be configured just like housing 20. The outlet section 372 and openings 376 are just like outlet sections 70 and openings 76, respectively. The helical shape of the biasing section creates a helical flow path 374 within the housing.

The piston section or member 352 is similar to piston section 92, in that it has a wedged shape opening 356 in the top of the piston member. In addition, however, the piston member 352 further includes a radial flow channel 358 cored out beneath the wedge shaped opening 356. As shown in FIG. 26, the flow channel 358 is wider in its cross-section than the opening 356 in the top of the piston member 352. Thus, even when the piston member 352 is forced into a round inlet channel in the housing 370, which causes the wedge shaped opening 356 to close, the flow channel 358 underneath is still partly open. As seen in FIG. 27, the wedge shaped opening 356 extends radially to one side of the piston member from a point which is between the centerline of the piston member and the opposite side of the piston member. The flow channel 358 extends from an even more distant point to the outside of the piston member 352. This flow channel 358 has been found to improve flow through the access device 350 when a syringe tip depresses the piston and biasing sections.

Two Y-site needlefree access devices 380 and 390 are shown in FIGS. 28 and 29, respectively. Both access devices are very similar, and use the same biasing and piston sections as in access device 350. The two access devices differ in the piece in which the secondary inlet is provided. In access device 380 a secondary inlet 382 is formed in the housing 384. The outlet section 386, biasing section 385 and piston section 383 are formed by a two shot molding process. The secondary inlet 382 is formed in a separate leg of the housing 384 than that which is used to house the biasing and piston sections. The housing 384 may be molded as one monolithic part with two legs, as shown, or it may be made from different parts that are then welded together. The housing 384 and outlet section 386 may be connected together with solvent welding or other well known techniques.

The access device 390 has the secondary inlet 392 formed in the outlet section 386. The housing 394 is just the same as housing 20. The outlet section 386 is sonically welded to housing 394 just as housing 20 and outlet section 70 are welded together.

The wedge shaped openings 387 and 397 in the top of the respective piston sections 383 and 393 are shown closed in FIGS. 28 and 29. However, the flow channels 389 and 399 underneath the openings still have a hollow section as shown because they are wider in cross-section than the wedge shaped opening, and therefore do not close up all the way when the elliptical piston section is forced into the inlet of the housing.

Another embodiment of a needleless access device 450 is shown in FIGS. 30, 30A, 31 and 32. The access device 450 is similar to the access device 350, in that it uses a solid biasing section with a helical shape on its outer surface. However, there are several significant differences between access devices 350 and 450. First, the number of revolutions or flights 465 on the helix is reduced, preferably to about 2.5 revolutions, and each flight is thinned out. The preferred thickness of each flight is different. As shown in FIG. 30A, the top flight is the thickest, at about 0.06 inches. The second flight is about 0.05 inches thick, and the third flight is about 0.040 inches thick. The thickness of the flights and other aspects of the helical shape are used to balance the spring force to get a good return while providing a good flow rate through the device. Second, the central area of the biasing section 460 was redesigned to increase its spring force by adding reverse cones 467 in its center between the flights 465. Third, the area above the wiper seal on the piston section 452 has a taper 451 (best seen FIG. 30A) that makes it easier for the piston section to reenter the inlet channel 473 of the housing 470 after the access device has been opened by a luer tip. Fourth, the intersection between the biasing section and the piston section, where the seal 454 is formed, was modified to be thicker, reducing the height of the piston section. The inside of the housing 470 at this point is also larger in diameter than housing 70, and does not have the tapered section as in previous embodiments, so that the inside of the housing matches the larger diameter of the top of the biasing section. Of course the housing 470 still has to be designed with a slight draft, less than ¼ of a degree, to make it so the part can be easily removed from the mold tool.

The outlet section 472 is also modified. As best seen in FIG. 32, the undercut 477 is increased, and the top 479 is made solid. The length of the sides 471 is longer, making the height of the shoulder 475 above flange 474 shorter. This increases the surface area of the contact between the resilient material making up the biasing section 460 and the thermoplastic material making up the outlet section 472. Holes 463 on both sides of the base of biasing section 460 are slightly larger than the holes 476 (best seen in FIG. 30) on both sides of outlet section 472. These holes allow flow into the center of outlet section 472. The mold tool that forms the perimeter of holes 463 can close off against the thermoplastic surrounding the holes 476 during the over molding of biasing section 460. The housing does not need a threaded section like the threaded section 35 in the housing 20. Rather, the base of the biasing section is flattened on the sides that mate up with holes 476 in the outlet section. After the helical flow around the piston section, the flow can split and go down either flat side into openings 463 and 476.

As best seen in FIG. 31, the piston section 452 may be formed with a flat 453 opposite the wedge shaped opening 456 and cored out flow channel 458. This flat is positioned at the beginning of the first flight of the helix. Once the piston section 452 is pushed down, the flat 453, the inside of the housing 470 and the position of first flight cooperate to form a flow path right into the beginning of the helical path between the flights 465. This helps to reduce the potential for the formation of a bubble at this point. In some earlier piston designs, a bubble would form at this point an not be flushed down the flow path.

While the preferred method of making the product is to use a two shot molding of the biasing section 460 onto the outlet section 472, the design of the needleless access device 450 can also be made by separately molding the biasing section 460 and the outlet section 472 and joining them together in a separate operation. While some of the benefits of the two shot, two piece product are not applicable to this method, the product can be made with conventional molding equipment, without the necessity of integrating thermoplastic and thermosetting molding technologies. Thus, the very functional needleless access device 450, having many desirable attributes, can be made even with conventional methods.

In the design of the access device 450 it has been found that the pitch of the helix, which is the linear distance from one crest to the next, will have an influence on the flow rate through the device. Currently a pitch of 0.25 inches has been found to work the best. The thickness of the flights is also important. Preferably the pitch and thickness of the flights cooperate to form a flow path within the housing and around the helix which is 0.04 inches wide.

Many of the desired attributes of a needleless access device are competing, making the optimal design difficult to achieve. For example, it would be nice to have a very resilient biasing section to provide a good return action, but this also increases the force required to open the device. Also, if a low durometer silicon is used to make the biasing section, a piston section made with the same low durometer silicon would tend to deform and occlude the syringe tip.

One possible solution to this problem is to cast the biasing and piston section in a two step molding process, where a stiffer (such as 80 durometer) thermosetting material is used to form the head and a softer (such as 30 durometer) thermosetting material is used to form the helical biasing section.

The design of the housing 470 and the flange 474 and shoulder 475 can be modified so that instead of using ultrasonic welding to connect the housing to the outlet section, a snap assembly could be used. The thermosetting material could then be molded so as to include a section that provides a gasket to help seal the needleless access device. The snap connection would preferably be able to withstand forces generated by an internal pressure of 500 psi.

Another difficulty encountered with some designs is that the biasing section is unable to return the piston section. A fine layer of oil or grease applied to the flights on the piston section can help to overcome friction between the flights and the wall of the housing. However, if the device is kept in use for a long time, or repeatedly actuated, the grease can be washed away. It may be beneficial to mold the piston section from a thermosetting material that is self lubricating, such as liquid silicone elastomer CSM-4970-3 from NuSil Technology, Carpinteria, Calf. 93013. Another possible solution to this problem is to provide a surface modification on the housing and/or piston section. While silicon has a high coefficient of friction on smooth thermoplastic surfaces, etching of the surfaces, or texturing the molds so as to produce a textured surface, could reduce the friction. However, one of the benefits of the helical flow path on the outside of the biasing section is that the user has visual access through a clear housing to see the flow path. Any etching or texturing of the inside of the housing would tend to make it more difficult to see through the housing. Thus it would be preferable to treat the silicone to reduce its friction. Such a treatment could include a sprayed on, baked coating available from GE Silicone Division of General Electric.

Several modifications to the shape of the piston section to increase flow rate are contemplated, as shown in FIGS. 33, 34 and 35. Each of these designs have the same biasing section 460 and sealing surface 454 as used in the embodiment of FIG. 30. However, in piston head 462 (FIG. 33), the relief 461 directly below the wiper seal has been added to make it easier for the wedge shaped opening 466 to close when the piston returns from being actuated. The depth of the flow channel 468 can also be modified to prevent collapse and improve flow. In the piston head 482, shown in FIG. 34, the area 485 at the base of the piston head is reduced in diameter. In the piston head 492 shown in FIG. 35, the wedge shaped opening 496 goes almost across the entire diameter of the top surface of the piston head.

Figure 36:
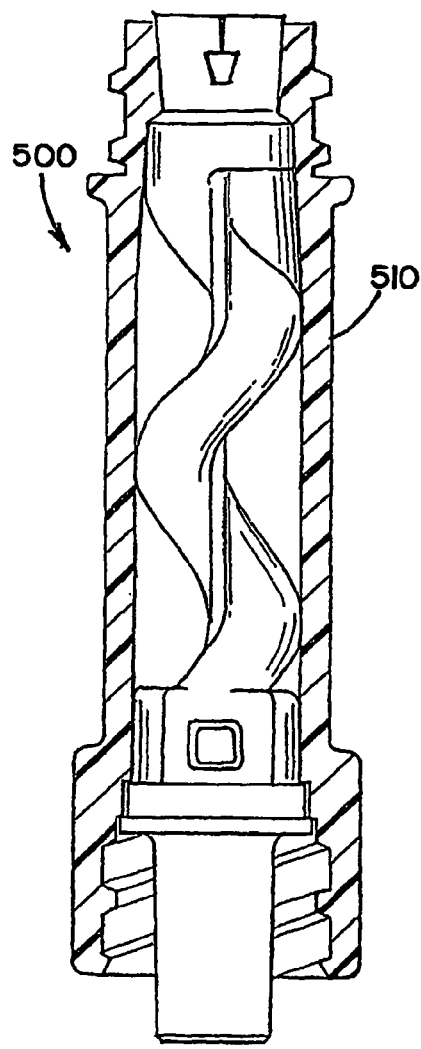
FIG. 36 is a partial cross-sectional view of a sixteenth embodiment of a needleless access device of the present invention shown in its closed position.

In the embodiment of FIG. 36, the needleless access device 500 is very similar to the embodiment of FIG. 30. The main difference is the length of the housing 510 and the pitch of the helix. It was thought that if the pitch of the helix were increased, and the housing length was also increased, flow rates through the device might be improved. However, testing of a device like that shown in FIG. 36, but with a short housing as in FIG. 30 and with a pitch of 0.358 inches, did not result in increased flow rates.

Figure 37:
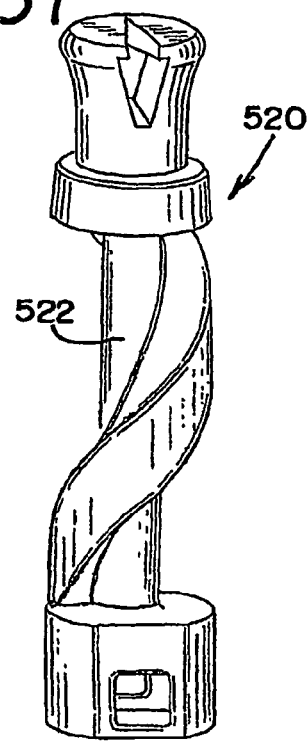
FIG. 37 is a perspective view of a seventeenth embodiment of combined biasing and piston sections of a flow control member of the present invention.

A different pitch for a helix is shown on the combined piston section and biasing section 520 shown in FIG. 37. In this design, only one revolution of the helix is used over the entire length of the biasing section. The center 522 of the biasing section is a fairly thick column.

Figure 38:
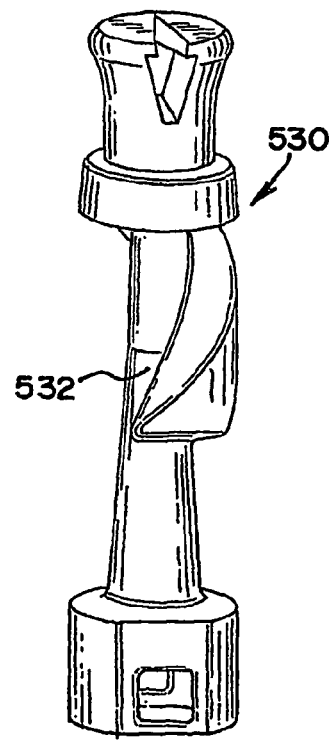
FIG. 38 is a perspective view of an eighteenth embodiment of combined biasing and piston sections of a flow control member of the present invention.
Figure 39:
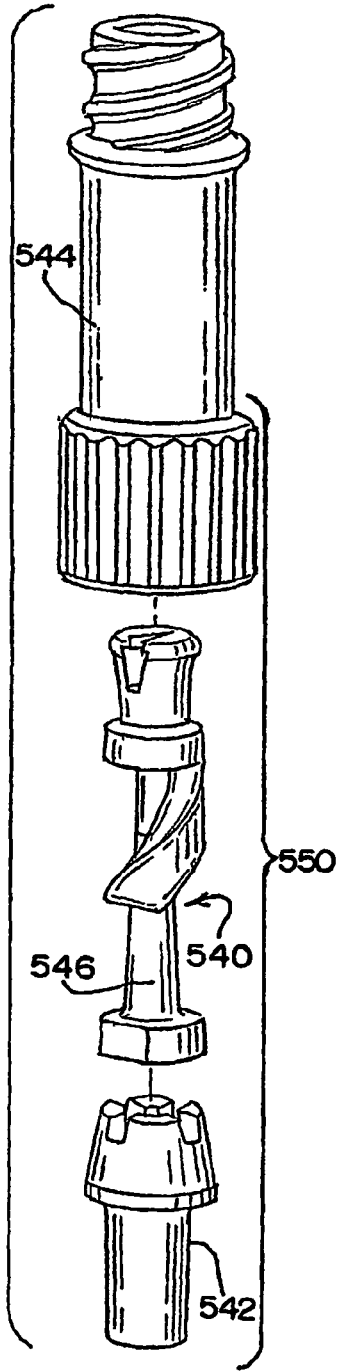
FIG. 39 is an exploded view of a needleless access device using a modified version of the combined biasing and piston sections of FIG. 38.

Another modified design is the combined biasing section and piston section 530 shown in FIG. 38. In this embodiment, the helix only has one-half of a revolution, and the center section 532 is conical in shape at the bottom. A slightly different embodiment, again with a half helix, is shown in FIGS. 39-41. The difference in this embodiment is that the bottom of the combined biasing section and piston section 540 is designed to sit on a separately formed outlet section 542, rather than be overmolded to it. In fact, in this embodiment the combined biasing and piston sections 540 need not be preassembled with the outlet section 542 when the needleless access device 550 is assembled. Instead, the combined sections 540 may be placed into the housing 544 and then the outlet section 542 secured to seal the base of the housing.

It is preferable with this design to have quite a significant preloading of the biasing section during the assembly. As seen in FIG. 40, the center column 546 deforms into a part helical shape itself when it is compressed into the housing 544. When the piston section 548 is forced into the housing 544 by syringe tip 18 (FIG. 41), the center column 546 further forms into a helix. Thus a helical flow path can be created even when the biasing section does not have a helical shape over its entire length.

FIG. 42 shows another embodiment of a combined piston and biasing section 560. While this design does not use a helical shape, nor form a helical flow path when placed inside a housing, it does use a piston section 562 with a wedge shaped opening 564 and a cored out flow channel 566 underneath just like the piston section 452 of FIG. 30. The flow path when the combined biasing and piston section 560 is used is over the accordion shape folds of the piston section. This design is less preferred because it does not create a single flow path, like that created with helical shape biasing sections. The biasing section can be solid or hollow, depending on the stiffness of the material of which it is made.

FIG. 43 shows a needleless access device 570 that is quite different from other embodiments shown previously, but can be made using the two shot molding method of the present invention. The needleless access device 570 is patterned after a device shown in U.S. Pat. No. 6,651,956, which is hereby incorporated by reference. The needleless access device 570 is a slit-type swabable luer-activated valve, but can be assembled from only two parts utilizing the present invention. Housing 572 can be molded as one part. Outlet section 574 can be molded from a thermoplastic in a first step, and overmolded with a thermosetting material 576 in a second step. The top portion of the thermosetting material 576 forms a piston that fits inside of the inlet section of housing 570. A slit 578 is provided in this piston section. The slit is normally closed. A hollow chamber 575 is formed in the thermosetting material 576 and extends into outlet section 574. When a syringe tip is forced against the thermosetting material 576, the material is forced downwardly and then expands outwardly, filling housing 572. The slit 578 opens so that fluid can be transferred through hollow chamber 575.

Figure 44A:
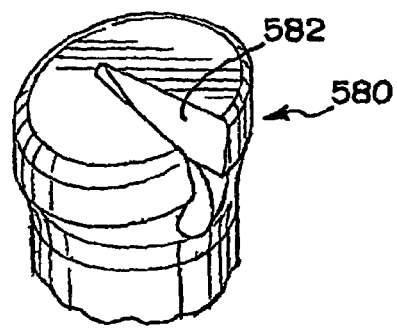
FIGS. 44A-44F are perspective views of six alternate embodiments of piston sections that could be used in the access device of FIG. 30.
Figure 44B:
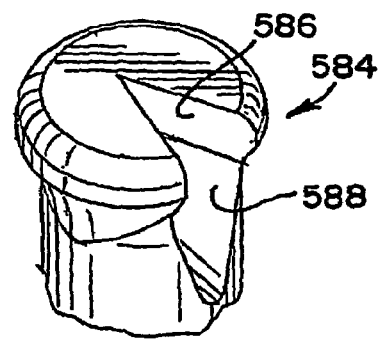
Figure 44C:
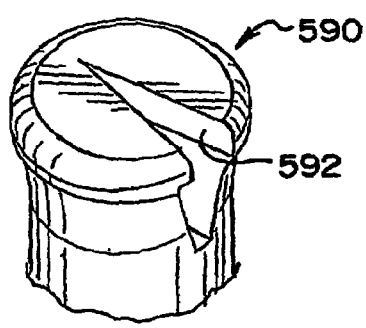
Figure 44D:
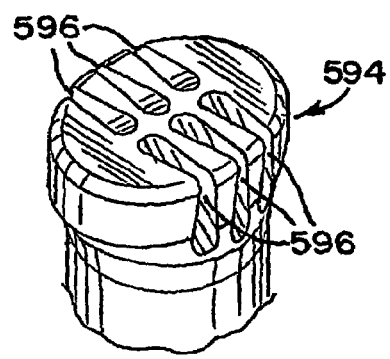
Figure 44E:
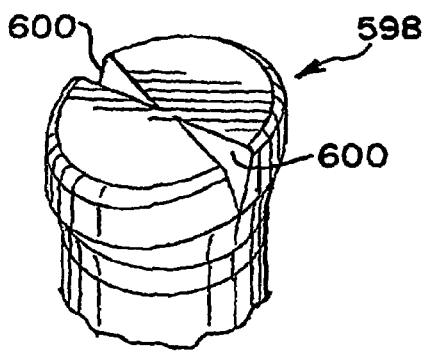
Figure 44F:
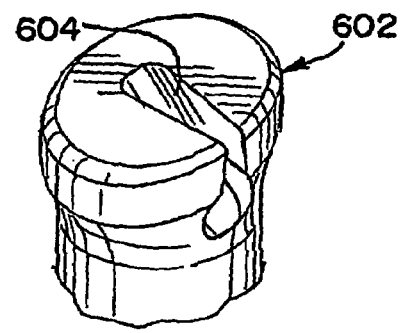

A variety of piston head designs are possible for use on needleless access devices of the present invention. FIGS. 44A-44F show several different embodiments, each with an elliptical shape in its uncompressed state and one or more openings to the side wall of the piston head. In piston head 580 (FIG. 44A), the wedge shaped opening 582 does not come to a point, but rather has a radius. As shown in FIG. 44B, piston head 584 has a wedge shaped opening 586. This embodiment differs in that the cored out flow channel 588 under the opening is deeper and the same width as the opening 586. FIG. 44C shows a piston head 590 that has a wedge shaped opening 592 that extends about ¾ of the way across the diameter of the head. FIG. 44D shows a piston head 594 with six openings 596, three on each side. The piston head 598 of FIG. 44E has two wedge shaped openings 600, one on each side of the piston head. FIG. 44F shows a piston head 602 with an opening 604 which is a reverse wedge, i.e., the opening is of a greater width in the center than at the perimeter.

Some of these designs may not be suitable if a syringe tip used with the piston head has a small central bore opening. For example, piston heads 594 and 598 could occlude the opening of a small bore syringe tip. Therefore products using these piston heads should specify the use of standard luer openings for mating connectors.

Figure 45:
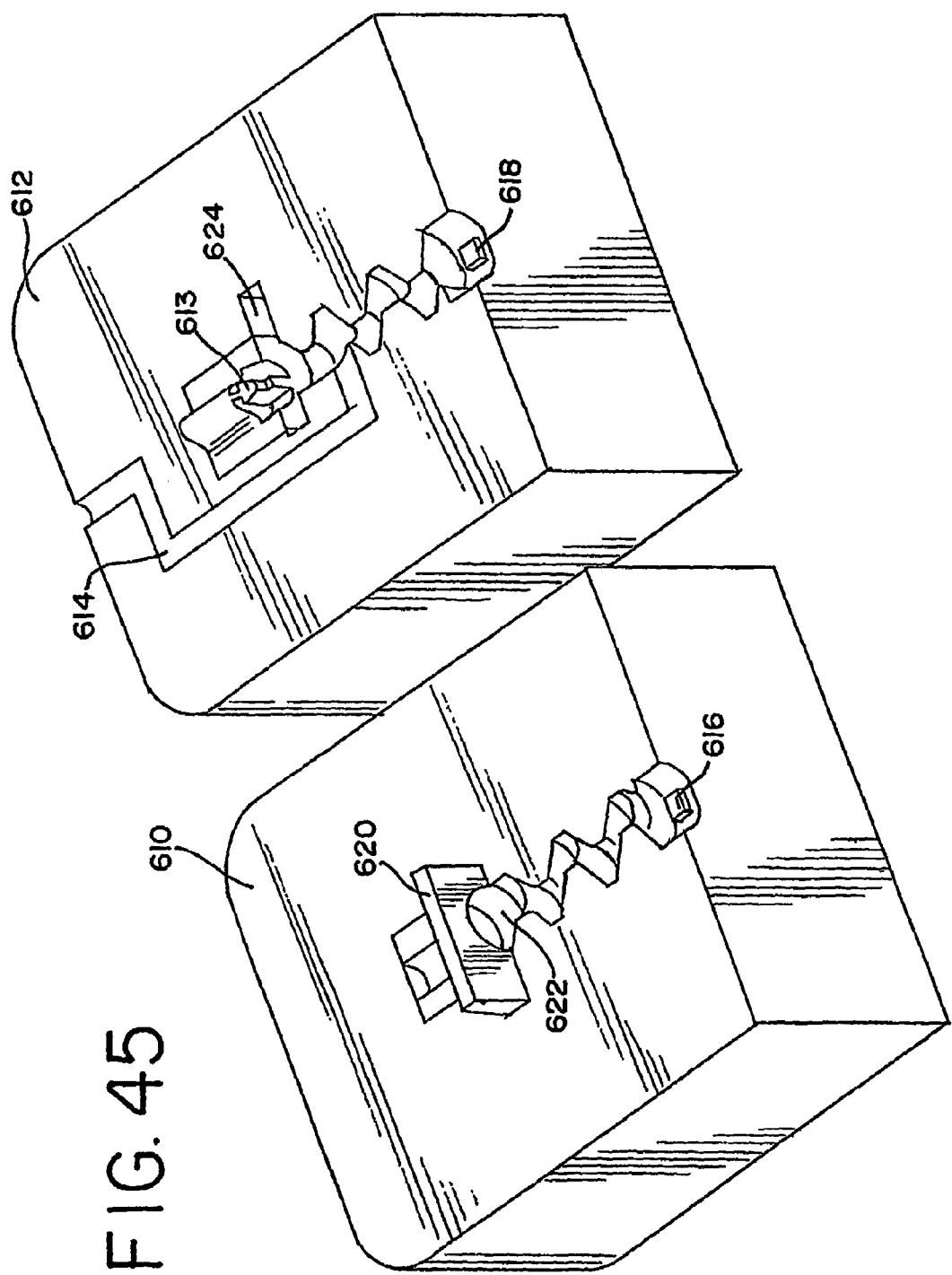
FIG. 45 is an opened, perspective view of two mold halves used to form the biasing and piston sections of the flow control member used in the access device of FIG. 30.

FIG. 45 shows a design for two mold halves 610, 612 to make the combined biasing and piston sections 460 and 452. The mold halves 610, 612 are cut to form cavities with the various features of the biasing and piston sections, such as the helical shapes to form the flights 465. Also protrusions 613 on mold half 612 form the wedge shaped opening 456 and cored out flow channel 458 in the piston section 452. A runner system 614 is used to feed the thermosetting material into the mold cavity when the two mold halves are closed on another. As noted earlier, lands 616 and 618 can close off against the sides of outlet section 472 around the holes 476 (FIG. 32) to form the holes 463. These holes allow flow from the outside helical flow path to enter the outlet section 472.

Because the surface 454 needs to form a good seal, it is preferable that it be formed as one continuous surface, without a part line that would normally be formed during an injection molding operation. For this reason, the mold halves 610, 612 are designed to form that section of the piston head without a part line. This is accomplished by using an insert 620 in mold half 610. The inside surface 622 of insert 620 forms the sealing surface 454. A cut 624 is made in the other mold half 612 for the insert 620 to fit into when the two mold halves are closed.

After the combined piston and biasing section is molded and cured, the mold halves are opened. The part will remain in mold half 610, surrounded by insert 620. The part has to be pulled downwardly through the hole 622 to be de-molded. Since the part is made of flexible, thermosetting material, it can deform slightly so that the elliptical shape of the top of the piston can fit through the hole 622.

Figure 46:
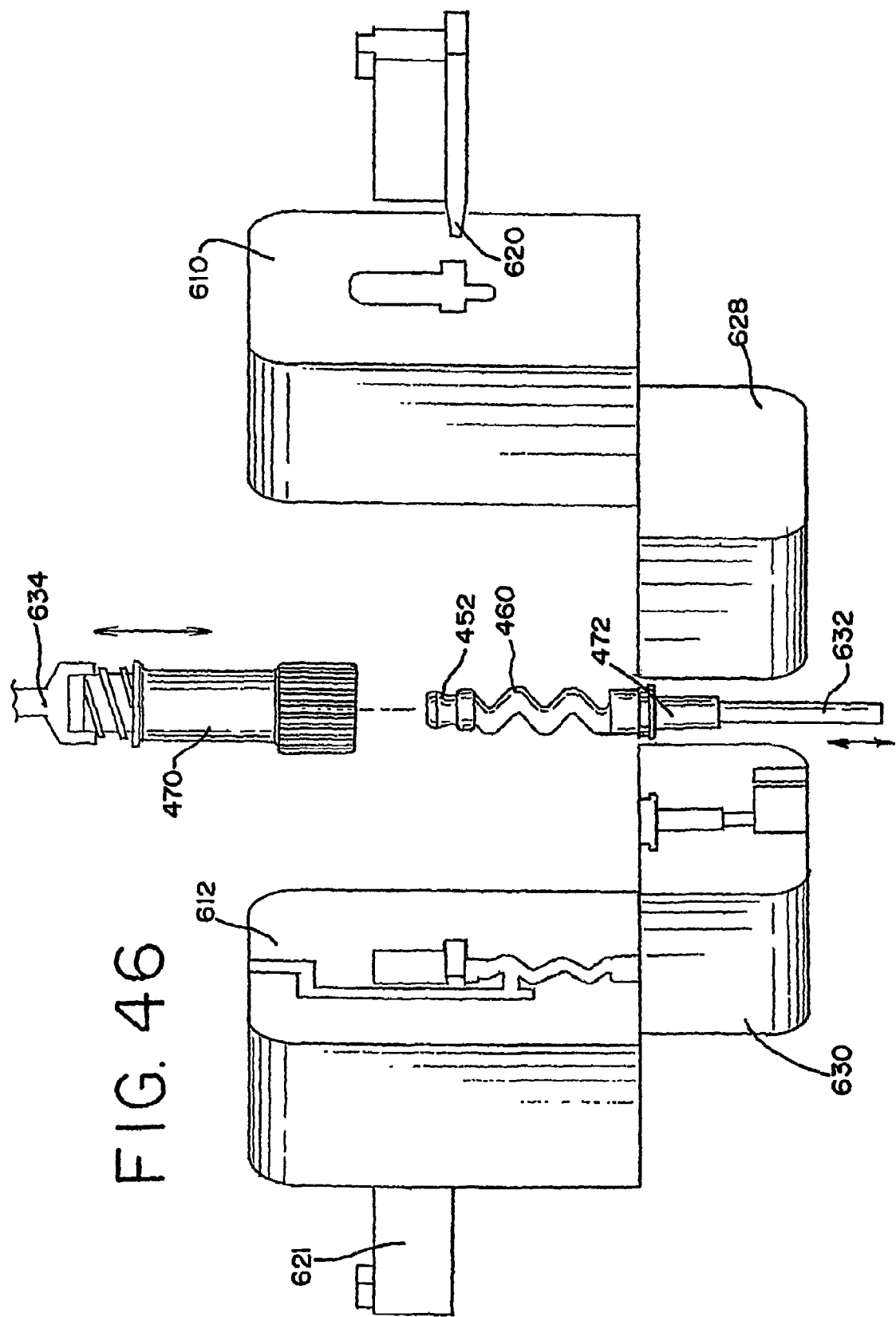
FIG. 46 is a schematic representation of the operation of the mold tools of FIG. 45 along with other mold tools used to make and assemble the access device shown in FIG. 30.

FIG. 46 schematically shown additional features about the mold tool that can be used to make the combined outlet, biasing and piston member used in the needleless access device 450. Mold halves 610 and 612 are used in the process. FIG. 46 shows that the detail, such as protrusions 613 which form the piston section, may be machined onto the insert 620 and a second insert 621 while the inserts are separated from the mold halves and thus more easily accessible. The inserts are shown in an exploded relationship in FIG. 46. However, after the inserts are machined, they are locked into place in mold tool halves 610 and 612 throughout further molding operations.

FIG. 46 shows the mold tools 628 and 630 and center core pin 632 that are used to first mold the outlet section 472. When this section is molded, there will be different mold tools (not shown) that will form the top of the outlet section, including the undercut 477, the top 479, the sides 471 and the holes 476. After the outlet section 472 is molded, it remains on the center core pin 632. Mold halves 628 and 630 are reused, and the mold halves used to form the top of the outlet section are replaced by mold halves 610 and 612, with the inserts 620 and 621 locked into place. The housing 470 is not present at this stage of the operation. The mold halves 628 and 630 are closed (or remain closed) and the mold halves 610 and 612 are closed. Silicone is injected into the cavity and the combined biasing and piston section 460, 452 is overmolded on the top of the outlet section 472, as shown. Mold half 612 is pulled back to the position shown in FIG. 46, and mold halves 628 and 630 are also opened. Center core pin 632 is then pulled downwardly to pull the piston section 452 through the hole 622 in insert 620. Thereafter the mold half 610 can also be pulled back to the position shown in FIG. 46.

At this point the center core pin can be raised back up and a housing 470 can be brought into place by robot arm 634. Once the pieces are aligned, the combined outlet, biasing and piston section are inserted into housing 470 and either snap assembled or welded together to form needleless access device 450.

The present invention also includes positive displacement needleless access devices. Needleless access device 130, shown in FIGS. 11 and 11A, has a positive displacement when activated, preventing the reflux of fluid when the piston section returns to its closed position. Three additional positive displacement needleless access devices, or parts thereof, are shown in FIGS. 47-51.

Positive displacement needleless access device 640 is shown in FIG. 47. In this embodiment, the biasing section is hollow, and is formed with number of accordion ribs 644. A chamber 646 is formed inside the device by a separate part 670. Two of the accordion ribs 648 are wider than the others and reach out far enough to contact the inside walls of the chamber 646. A vent 650 leads out of the chamber 646 and vents into the area of the luer-lock threads inside the base of housing 652. As the piston head 654 is activated, the biasing section 642 accordion folds, and ribs 648 force air out through the vent 650. When the piston is released, the biasing section 642 forces the piston back up into the inlet section of housing 652, and air can return through vent 650 into the bottom of chamber 646. The piston head 654 includes a wiper seal 656. However, rather than a wedge shaped opening into the side of the piston head, the piston head has a flattened V shaped top surface. The inlet of housing 652 has several flow channel 658 formed in its sidewall. Thus fluid can flow over the top of the piston head once the piston head is depressed past the tops of the flow channels 658. Flow continues downwardly around the outside walls of part 670 forming chamber 646 and then radially inwardly through channel 672 into the interior of outlet section 674. The outlet section 674 can be molded from the same resilient material as is used to form the biasing section 642 and piston head 654, or more preferably the part can be molded from a thermoplastic and the biasing section overmolded from a resilient thermosetting material. Unfortunately, it would be too difficult to also mold the part 670 which forms the chamber 646 with the other biasing section 642. Thus even though this design can utilize two-shot aspects of the invention, it would still require three separate pieces to be assembled.

A flow control member 680 used to make another positive displacement needleless access device is shown in FIG. 48. This part is molded from a resilient material as one monolithic piece. It can be inserted into a housing like housing 652 to create a needlefree access device. Mold tool core elements create voids 682 in the part 680 when it is molded and the core elements are withdrawn, much like the voids 149 in the device 130 of FIG. 11. Outlet channel 684 is molded using a transverse core pin. Also, cavity 683 extends completely through the part, like the openings 142 in FIG. 11. Once the part is assembled in the housing, the fluid flow path is around the outside of the part and then inwardly through channel 684 to the interior of the outlet section 686. However, when the piston section is depressed, the voids 682 can collapse, allowing air to flow to the exterior of the device through the area of the luer-lock, just as in access device 640. When the piston is released, air can travel back in to fill the voids 682. These voids thus allow the piston to return without causing reflux through the outlet section. The cavity 683 fills with fluid, since it is open to the outside of the member. A small bridge 685 of material is designed to help prevent the outlet channel 684 from collapsing when the device is actuated. This bridge is formed by a gap between the pointed top of the core pin (not shown) used to form the opening in the center of outlet section 686 and the bottom of the side slides (not shown) in the mold tool that create cavity 683.

Positive displacement needleless access device 690 is shown in FIGS. 49-51. This device is made from three separate parts, a housing 692, flexible biasing and piston member 694 and a base outlet section 696. The biasing and piston member 694 is placed on top of base outlet section 696, and this combination is then inserted into housing 692. The biasing and piston member 694 includes an elliptical top shape with a wedge shaped opening 698, just like the piston section 97 of piston section 93 shown in FIG. 9. Inside of the biasing and piston member 694 is an air chamber 700, which is vented to the outside through four channels 702 found in base 696, best seen in FIG. 49. The top side of the base outlet section 696 includes a relief 697 cut into it (see FIG. 50) that connects the four vent channels 702. This relief prevents the biasing and piston member 694 from blocking the vent channels 702 when it collapses. One or more flow channels 704 are cut in the side wall of housing 692 (see FIGS. 49 and 51). When the piston section is pushed down by syringe tip 18 to the point shown in FIG. 51, the chamber 700 collapses, with air flowing out of channels 702. Flow from the syringe can then pass through opening 698 into channel 704. Base 696 also includes a transverse flow channel 706. Thus fluid can travel from flow channel 704 into channel 706 and out through outlet 708. When the syringe tip is withdrawn, biasing section 694 pushes the piston head back into the inlet channel of housing 692. Air can return to fill the chamber 700 through the channels 702.

Another form of a needless access device 710 is shown in FIG. 52. This device is like the Y-site devices 380 and 390 in that the housing 712 has two inlets 714, 716 and one outlet 718. In this embodiment, flow can continue through the device from inlet 714 to outlet 718 regardless of the position of biasing and piston member 720. However, inlet 716 is designed like the top part of access device 450, in that the piston section 722 normally seals the inlet, but can be opened by insertion of a syringe tip to give access to inlet 716. The biasing section 724 is made with a helical design, creating a helical flow channel within the branch of the housing containing the biasing section 720.

This embodiment can be made with two shot molding and two piece assembly. The first part of the housing can be made with an opening into which a second part of the housing 726 fits to complete the housing. This second part of the housing can be molded first from a thermoplastic material, and then the biasing and piston member 720 overmolded onto it. The overmolded part is then inserted into the first part of the housing and either snap assembled or ultrasonically welded to complete the device 710. In this embodiment, the part of the housing to which the thermosetting material is overmolded does not form an outlet to the housing.

As noted above, in addition to needleless access devices, aspects of the present invention are also applicable to check valves. Two embodiments of check valves are shown in FIGS. 53 and 54.

A first embodiment of a check valve 801 is schematically shown in FIG. 53. The check valve 801 has three main elements, namely, a first housing part 802, a second housing part 804 and a diaphragm 806 constituting a sealing member positioned between these two housing parts. The diaphragm constitutes a flow control member. Each of the housing parts includes a connector, and is made by injection molding a thermoplastic material. Housing part 802 is designed as a hose connector, but also includes a female luer taper 842 in its inlet 840. Housing part 804 includes an outlet 821 in the form of a male luer-lock fitting 822.

The first housing part 802 includes an annular sealing surface 808 against which the diaphragm 806 is pretensioned. The check valve 801 is especially suitable for medical fluids, but could be used in other fields, such as in the fields of micro pneumatics and micro hydraulics.

The diaphragm 806 can be lifted from the sealing surface 808 with sufficient overpressure in entry space 810 of the first housing part 802, thus creating a flow path through the device. With an overpressure in an exit space 812 of the second housing part 804, the diaphragm 806 safely and in minimal time can be pressed against the sealing surface 808 for closing the check valve 801.

As shown in FIG. 53, the diaphragm 806 is connected with the second housing part 804 in a way that the second housing part 804, together with the diaphragm 806, can be handled as a unit when being assembled with the first housing part 802. Preferably the diaphragm 806 is overmolded to the second housing part 804 by the overmolding of a sealing member 816, of which the diaphragm 806 is an integral part. The sealing member projects into the exit space 812 of the first housing part 802 in such a way that the diaphragm 806 is pretensioned against the sealing surface 808.

The diaphragm 806 preferably comprises a thermosetting material, preferably silicon, or a thermoplastic elastomer.

In the preferred embodiment shown in FIG. 53, the first housing part 802 includes a skirt 818 reaching far downwardly which almost completely surrounds the second housing part 804. As a result, the sealing surface 808 is completely protected and deeply positioned within the first housing part 802.

As shown in FIG. 53, the second housing part 804 has a T-shape cross-section, wherein the upright member 820 of the T is formed as a male luer-lock-connector 822. The skirt 818 has an interior thread for a possible nut connection. The cross member 824 of the T-shaped second housing part 804 forms a wall connected with the interior side of the skirt 818 in a fluid-tight manner.

On the top side 828 of that wall a basically cylindrical body 830 is monolithically formed with the rest of the second housing part 804. The cylindrical body 30 contains a channel 832 for fluid to flow out of the outlet 821. The sealing member 816 has a cup-shaped bottom section 834 which is overmolded around the cylindrical body 30. A stem-shaped extension 836 connects the monolithic disk-shaped diaphragm 806 with the cup-shaped bottom section.

In case the pressure in the exit space 812 should become larger than in the entry space 810, then the pressure of the fluid against the diaphragm 806 will keep the diaphragm 806 engaged against the annular sealing surface 808, preventing any reflux. This happens, too, if the fluid flow at the entrance 840 stops.

In addition to normally closed check valves, the present invention is applicable to check valves wherein the sealing member, while still being adjacent the sealing surface, is not necessarily pretensioned. The check valve would still close if fluid tried to flow backwards through the device.

The check valve 802 can be made by a two shot molding process. The housing part 802 is injection molded from a thermoplastic material, preferably chosen from the group consisting of polycarbonates, polysulfones, nylons and acrylic resins. The first housing part having the annular sealing surface 808 in the inlet space 810 either is ejected from the mold after the solidification or is retained in the open mold in case an assembly within the injection molding machine is planned. The second housing part 804 is also injection molded from a suitable thermoplastic material in a second injection mold, wherein the mold has a bottom part and a first top part. The first top part molds the bypass channels 832. Once it is removed, with the second housing part 804 remaining in the bottom part of the mold, a second top part of the mold is positioned on the bottom part of the mold. The second top part of the mold has a mold cavity corresponding to the diaphragm 806, the bottom section 834 and the extension 836. Thereafter the elastic material is injected into the second mold with the second top part thereon.

The unit produced thereby, consisting of the second housing part 804 and diaphragm 806, can thereafter either be ejected from the second mold and thereafter assembled with the first housing part, e.g. by ultrasonic welding, or by suitable measures an assembly within the injection molding machine can follow by bringing the bottom part of the first injection mold, still containing the first housing part 802, together with the bottom part of the second injection mold, which still contains the unit consisting of the diaphragm 806 and the second housing part 804. Suitable ejector pins advance the second housing part 804 together with the diaphragm 806 into the space surrounded by the skirt 818 until the wall reaches a step of the skirt 818 and is assembled with the first housing part 802 in a fluid tight manner, such as by ultrasonic welding.

One of the benefits of the check valve 801 is that it can be assembled from merely two parts. Further, a final assembly within the injection molding machine is possible.

A second embodiment of a check valve 831 is shown in FIG. 54. This check valve is very similar to the needleless access device 710 with respect to the housing, and uses very similar parts as check valve 801 with respect to the diaphragm 806 and sealing surface 808.

The check valve 831 also has an injection molded housing made of two parts, each made of suitable thermoplastic material. It has two inlets 846 and 848 and one outlet 850. The inlet 846 is positioned coaxial to the outlet 850. The second inlet 848 basically is normal to the common axis of the inlet 846 and the outlet 850.

The inlet 848 is controlled by the check valve generally designated with 844. The connection between the first inlet 846 and the outlet 850 and the second inlet 848 is by means of a common valve chamber 854. The valve chamber 854 is closed by a cover 856 (which constitutes a second housing part) of a thermoplastic material positioned opposite to the second inlet 848.

The check valve includes an annular sealing surface 809 surrounding the second inlet 848 against which a diaphragm 807 of resilient material is pretensioned.

According to the basic principle of the invention, the diaphragm 807 is connected with the cover 856 in such a way that the cover 856 and the diaphragm 807 can be handled as a unit when being assembled with the housing to form the check valve 831.

As with the first embodiment according to FIG. 53, the diaphragm 807 is connected with the cover 856 by overmolding. In this embodiment, the resilient thermosetting material has a stepped cylindrical shape, matching that of the cover member 856, and also forms the diaphragm 807.

The check valve 831 is formed with a male luer-lock-connector for outlet 850. The first inlet 846 is formed as a female luer-lock-connector such that the check valve 831 can be coupled with one or more check valves of the same kind in a row. Thereby a through-line can be formed having a number of inlets 848 each controlled by a check valve 844 without a complicated housing and the corresponding costs for the mold to make such a housing.

The check valve 831 is produced by first forming the T-shaped housing by injection molding a thermoplastic material in a first mold. After the solidification of the thermoplastic material, the finished housing either is ejected from the mold or can be retained in the injection molding machine in one of the mold halves in a suitable position for final assembly. In a second split injection mold consisting of a bottom part and first top part, the cover 856 with the cylindrical projections is molded from a thermoplastic material and thereafter the first top part of the mold is removed, wherein the cover 856 with the cylindrical projections remains in the bottom part of the mold. Thereafter a second top part of the mold is positioned on the bottom part of the mold, the second top part of the mold having a mold cavity corresponding to the diaphragm 809, the bottom sections and the extension. An elastic material, such as a thermo-setting material like silicon, or a thermoplastic elastomer, is injected into the mold.

After the solidification, either the unit consisting of the cover 856 and the diaphragm 807 can be ejected from the bottom part and can be assembled with the housing, or as with the embodiment of FIG. 53 a final assembly can take place within the injection molding machine by keeping the unit consisting of the diaphragm 807 and the cover 856 in the bottom part of the second mold and bringing it together with the housing remaining in the mold half of the first mold and directly assembling these parts by ultrasonic welding.

In addition to the fact that the preferred access device may be assembled from only two parts, and thus have a lower manufacturing cost, the access device can also be made with higher quality control because of its fewer parts. Some of the functional requirements that are met by the preferred embodiments of the invention are as follows. In addition to being low cost because of the two part construction, the preferred access devices have an internal priming volume of less than 0.3 ml, more preferably less than 0.1 ml. After a flush procedure using 1.5 ml of saline solution, the residual fluid in the access device should be less than 10% of the priming volume, preferably less than 2% of the priming volume. The preferred access devices have a flow rate, measured at 39" water head pressure, of greater than 100 ml/min., more preferably greater than 140 ml/min. The access devices can preferably be activated at least 100 times, and more preferably at least 200 times, and retain their ability to reseal. In this manner one access device can be used on a patient that may need a large number of injections each day for several days.

The preferred access devices can withstand an internal pressure of at least 100 psi, and more preferably at least 300 psi, and a negative pressure of at least 12.5 psi and more preferably at least 14 psi. The wiper seal on the preferred connection will be able to prevent bacterial ingress for at least 24 hours, and more preferably at least 96 hours. Preferably the top wiper seal, in addition to preventing bacterial ingress, can withstand a pressure of 2 psi. The preferred access devices will have luer tapers on both the male and female connections, and be compatible with components that meet ISO 594-2 and ISO 494-2 standards, meaning that the access device male and female connections have the same diameter and 6% taper angle, but not necessarily the same length, as the ISO standards. However, they will preferably still provide contact over at least 0.1 inches of length, but not necessarily the 0.25 inch length contact of a standard luer taper. The preferred access devices are luer slip as well as luer lock compatible.

The amount of biasing force provided by the biasing member will preferably be at least 0.2 lbs, and more preferably at least 0.5 lbs, but will produce an activation force of less than 3.5 lbs, and more preferably less than 2.5 lbs. The preferred access devices have less than 30% flow reduction, and preferably less than 10% flow reduction, after 100 activations. The preferred access devices have a return time of less than 1 second, more preferably less than 0.5 seconds.

The preferred access devices will be made from materials that are compatible with a full range of fluids and antiseptics that are likely to come in contact with the access devices, such as high dextrose fluids, blood plasma, lipid emulsions, taxol and other chemotherapy drugs, and providone iodine, chlorhexidine and isopropyl alcohol antiseptics. The access devices will also preferably be compatible with various other medical devices, such as IV pumps, as well as gravity infusion, vacuum containers, jet injectors, IV sets and can withstand MRI fields. The preferred access devices can be sterilized by electron beam, steam, gamma radiation and ethyl oxide gas.

As will be appreciated, making a device such as the preferred embodiment of the invention that meets all of the above requirements, can be made with higher quality control, and can still be made at a low cost, is a considerable achievement. In addition, the preferred device is small, less than 1.3 inches, and preferably less than 1 inch in length.

It should be appreciated that the apparatus and methods of the present invention are capable of being incorporated in the form of a variety of embodiments, only a few of which have been illustrated and described above. For example, the central portion of the biasing section 60 could have a small diameter central hollow area, have a different pitch in the helical groove, be longer or shorter, etc. Also, rather than using a sonic or solvent weld to connect the housing with the flow control member, a snap-lock feature could be used. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes that come within the meaning and range of equivalency of the claims are to be embraced within their scope.

We claim:

1. A needlefree access device comprising:
   a) a housing having an inlet, a base comprising an outlet, and a main body portion having a generally cylindrical inside surface between the inlet and the base;
   b) a valve member actuatable between an open position and a closed position, the valve member comprising a piston section that includes a wiper seal adjacent the inlet when the valve member is closed, wherein in the closed position the valve member prevents flow between the inlet and the outlet, and wherein the piston section further comprises an opening in the top thereof, and a flow channel beneath and connected to the opening and extending radially to the outside of the piston section; and
   c) a central body within the main body portion of the housing, the central body having a helical shape on its outer surface, the central body fitting against the inside of the cylindrical surface when the valve member is in its open position;
   d) the helical shape defining a helical flow path through the main body portion of the housing when the valve member is in an open position.

2. The needlefree access device of claim 1 wherein the device is suitable for transferring medical fluids.

3. The needlefree access device of claim 1 wherein the piston section is made from a resilient material.

4. The needlefree access device of claim 1 wherein the opening is a wedge shaped opening that extends radially to one side of the piston section from a point which is between the centerline of the piston section and the opposite side of the piston section.

5. The needlefree access device of claim 1 wherein the housing further comprises a tapered inlet channel having a luer taper for engaging with a syringe tip having a luer taper.

6. An IV bag having a port comprising a needlefree access device as recited in claim 1.

7. The needlefree access device of claim 1 wherein the wiper seal closes the inlet against airborn bacteria when the valve member is in the closed position.

8. The needlefree access device of claim 1 wherein the flow channel has a cross-sectional area larger than that of the opening in the top of the piston.

9. A needlefree access device comprising:
   a) a housing having an inlet, base comprising an outlet, and a main body portion having a generally cylindrical inside surface between the inlet and the base;
   b) a valve member actuatable between an open position and a closed position, wherein in the closed position the valve member prevents flow between the inlet and the outlet; and
   c) a central body within the main body portion of the housing, the central body having a helical shape on its outer surface, the central body fitting against the inside of the cylindrical surface when the valve member is in its open position;
   d) the helical shape defining a helical flow path through the main body portion of the housing when the valve member is in an open position
   wherein the valve member is formed as part of a piston section of a combined piston section and biasing section.

10. The needlefree access device of claim 9 wherein the central body forms part of the biasing section.

11. The needlefree access device of claim 9 wherein the combined piston and biasing section comprises resilient material and is overmolded onto an outlet section comprising thermoplastic material, which in turn is attached to the base of the housing.

12. The needlefree access device of claim 11 wherein the resilient material has a Shore A durometer of between about 30 and 90.

13. A needlefree access device comprising:
   a) a housing having an inlet, an inlet channel and an outlet; and
   b) a biasing and piston member having
      i) a piston section moveable between a closed position in which the piston section is in the inlet channel and an open position in which the piston section is inside the housing below the inlet channel but allows fluid to flow through the inlet channel; and
      ii) a biasing section connected to the piston section that normally biases the piston section into the inlet channel, the biasing section comprising a resilient body having a helical shape on at least part of its outer surface, the helical shape cooperating with the housing surrounding the biasing section to provide a helical flow channel through the device.

14. The needlefree access device of claim 13 wherein the device is suitable for handling medical fluids.

15. The needlefree access device of claim 13 wherein the inlet channel comprises a female luer taper.

16. The needlefree access device of claim 13 wherein the piston section in its closed position seals the inlet channel against airborne bacteria.

17. The needlefree access device of claim 13 wherein the piston section in its closed position is either flush with or extends out of the housing inlet.

18. The needlefree access device of claim 13 wherein the biasing section has a solid central section.

19. The needlefree access device of claim 13 wherein the biasing section is generally hollow.

20. The needlefree access device of claim 13 wherein the helical flow channel has a cross-sectional width of about 0.02 inches when the piston section is in its open position.

21. The needlefree access device of claim 13 wherein the helical flow channel has a cross-sectional width of about 0.04 inches when the piston section is in its open position.

22. The needlefree access device of claim 13 wherein the piston section comprises a normally elliptical top portion with a wedge shaped opening therein.

23. The needlefree access device of claim 22 wherein the housing inlet is round and the biasing and piston member is deformable such that when the piston section is in its closed position, the top portion is forced into a round shape and the wedge shaped opening is closed.

24. The needlefree access device of claim 23 wherein the piston section further comprises a radial flow channel beneath the wedge shaped opening.

25. The needlefree access device of claim 13 wherein the housing comprises a generally smooth cylindrical wall surrounding the biasing section.

26. The needlefree access device of claim 25 wherein the housing further comprises an internal threaded section adjacent the connection between the biasing section and the outlet section.

27. The needlefree access device of claim 13 wherein the resilient body of the biasing section is made with a material that has a Shore A durometer of between about 50 and about 80.

28. The needlefree access device of claim 13 where in the piston section includes a wiper seal.

29. The needlefree access device of claim 28 wherein the wiper seal can withstand a pressure of at least 2 psi.

30. The needlefree access device of claim 28 wherein the wiper seal closes the inlet against airborn bacteria when the piston section is in the closed position.

31. The needlefree access device of claim 13 wherein the piston section and biasing section are formed as one monolithic piece.

32. The needlefree access device of claim 31 wherein the monolithic piece is overmolded onto a section of the housing forming the outlet to provide a combination outlet, biasing and piston member.

33. The needlefree access device of claim 13 wherein the biasing section provides a force of between about 0.2 lbs and about 3.5 lbs.

34. The needlefree access device of claim 13 wherein the piston section comprises a normally elliptical top portion with a V-shaped opening across a minor axis of the ellipse.

35. The needlefree access device of claim 13 wherein the piston section has a top surface that extends above the inlet.

36. The needlefree access device of claim 35 wherein the top surface of the piston section is slanted and extends above the inlet on only one side of the access device.

37. The needlefree access device of claim 13 wherein the housing includes threads for a luer lock fitting in the area surrounding the inlet channel.

38. The needlefree access device of claim 13 wherein the housing comprises a base with threads for forming a luer lock.

39. The needlefree access device of claim 13 wherein the housing comprises an internal sealing surface and the piston section seals against the sealing surface to prevent backflow through the access device when the piston section is in its closed position.

40. The needlefree access device of claim 13 wherein the top portion of the piston section has a V-shaped opening therein.

41. The needlefree access device of claim 13 wherein the needlefree access device is in the form of a Y-shape access device, and comprises a secondary inlet.

42. The needlefree access device of claim 41 wherein the secondary inlet is formed in the housing.

43. The needlefree access device of claim 41 wherein the secondary inlet is formed in the outlet section.

44. The needlefree access device of claim 13 wherein the helical shape comprises at least one complete helical revolution.

45. The needlefree access device of claim 13 wherein the helical shape comprises less than one complete helical revolution.

46. The needlefree access device of claim 13 wherein the housing is made of a housing member and an outlet member secured to the housing member and providing the outlet thereof.

47. The needlefree access device of claim 46 wherein the outlet member comprises an outlet section interlocked to the biasing section and having an outlet fitting in fluid communication with the inside of the housing; wherein the piston section, biasing section and outlet section are connected together such that they can be handled as one piece when assembled with the housing to make the needlefree access device.

48. The needlefree access device of claim 47 wherein the connected outlet section, biasing section and piston section comprise thermoplastic material and resilient material.

49. The needlefree access device of claim 48 wherein the resilient material is overmolded onto the thermoplastic material.

50. The needlefree access device of claim 48 wherein the resilient material is a resilient thermosetting material.

51. The needlefree access device of claim 50 wherein the thermosetting material comprises silicone.

52. The needlefree access device of claim 48 wherein the resilient material comprises thermoplastic elastomer.

53. A needlefree access device comprising:
a) a housing having an inlet, a base comprising an outlet, and a main body portion having a generally cylindrical inside surface between the inlet and the base;
b) a valve member actuatable between an open position and a closed position, the valve member comprising a piston section that includes a wiper seal adjacent the inlet when the valve member is closed, wherein in the closed position the valve member prevents flow between the inlet and the outlet; and
c) a central body within the main body portion of the housing, the central body having a helical shape on its outer surface, the central body fitting against the inside of the cylindrical surface when the valve member is in its open position;
d) the helical shape defining a helical flow path through the main body portion of the housing when the valve member is in an open position;
wherein the piston section comprises a normally elliptical top portion with a V-shaped opening across a minor axis of the ellipse.

54. A needlefree access device comprising:
a) a housing having an inlet, a base comprising an outlet, and a main body portion having a generally cylindrical inside surface between the inlet and the base;
b) a valve member actuatable between an open position and a closed position, the valve member comprising a piston section that includes a wiper seal adjacent the inlet when the valve member is closed, wherein in the closed position the valve member prevents flow between the inlet and the outlet; and
c) a central body within the main body portion of the housing, the central body having a helical shape on its outer surface, the central body fitting against the inside of the cylindrical surface when the valve member is in its open position;
d) the helical shape defining a helical flow path through the main body portion of the housing when the valve member is in an open position;
wherein the piston section in its closed position is either flush with or extends out of the housing inlet.

55. A needlefree access device comprising:
a) a housing having an inlet, a base comprising an outlet, and a main body portion having a generally cylindrical inside surface between the inlet and the base;
b) a valve member actuatable between an open position and a closed position, the valve member comprising a piston section that includes a wiper seal adjacent the inlet when the valve member is closed, wherein in the closed position the valve member prevents flow between the inlet and the outlet; and
c) a central body within the main body portion of the housing, the central body having a helical shape on its outer surface, the central body fitting against the inside of the cylindrical surface when the valve member is in its open position;
d) the helical shape defining a helical flow path through the main body portion of the housing when the valve member is in an open position;

wherein the piston section comprises a normally elliptical top portion with a wedge shaped opening therein.

56. The needlefree access device of claim 55 wherein the housing inlet is round and the piston section is moveable in the housing inlet and is deformable such that when the piston section is in its closed position, the top portion is forced into a round shape and the wedge shaped opening is closed.

* * * * *